US010258785B2

(12) United States Patent
Mide et al.

(10) Patent No.: US 10,258,785 B2
(45) Date of Patent: Apr. 16, 2019

(54) DISCONNECTING MECHANISMS

(71) Applicant: CONCEPTOMED AS, Ballstad (NO)

(72) Inventors: Christian Mide, Ballstad (NO); Marius Andresen, Oslo (NO); Rolf Blomvågnes, Rong (NO); Kevin Geers, Oslo (NO)

(73) Assignee: CONCEPTOMED AS, Ballstad (NO)

( * ) Notice: Subject to any disclaimer, the term of this patent is extended or adjusted under 35 U.S.C. 154(b) by 0 days.

(21) Appl. No.: 15/892,598

(22) Filed: Feb. 9, 2018

(65) Prior Publication Data
US 2018/0200499 A1 Jul. 19, 2018

Related U.S. Application Data

(63) Continuation-in-part of application No. 14/905,978, filed as application No. PCT/EP2014/066436 on Jul. 30, 2014, now Pat. No. 9,889,259.

(30) Foreign Application Priority Data

Nov. 29, 2013 (GB) .................................. 1321128.9

(51) Int. Cl.
*A61M 39/10* (2006.01)
(52) U.S. Cl.
CPC .... *A61M 39/1011* (2013.01); *A61M 39/1055* (2013.01); *A61M 2039/1016* (2013.01); *A61M 2039/1033* (2013.01)

(58) Field of Classification Search
CPC .... A61M 5/31; A61M 5/3134; A61M 5/3205; A61M 5/347; A61M 39/1011;
(Continued)

(56) References Cited

U.S. PATENT DOCUMENTS 2,047,512 A 7/1936 Kauffman
2,875,760 A 3/1959 Haber
(Continued)

FOREIGN PATENT DOCUMENTS

DE 883053 C 7/1953
DE 29707813 U1 7/1997
(Continued)

*Primary Examiner* — Imani N Hayman
*Assistant Examiner* — Tiffany Legette
(74) *Attorney, Agent, or Firm* — Eversheds Sutherland (US) LLP

(57) ABSTRACT

A disconnecting mechanism includes a main body including a fluid transfer tip having a tapered surface to form a friction fit with a corresponding connector. The lever member includes a threaded portion to enable the corresponding connector part to be connected to the fluid transfer tip by a screw fit in addition to the friction fit, and an actuator portion to actuate release of the friction fit. In a first pivotal position, the threaded portion has a first position close to the fluid transfer tip to engage with an outer thread or rim of the corresponding part and thereby form the screw fit in addition to the friction fit. In a second pivotal position, the threaded portion has a second position further away from the fluid transfer tip to disconnect the screw fit and the actuator portion is moved forward to push the connector part and release the friction fit.

20 Claims, 18 Drawing Sheets

(58) Field of Classification Search
CPC ...... A61M 39/1055; A61M 2039/1016; A61M 2039/1033
See application file for complete search history.

(56) References Cited

U.S. PATENT DOCUMENTS

| | | | |
|---|---|---|---|
| 4,425,119 A | 1/1984 | Berglund | |
| 4,490,142 A | 12/1984 | Silvern | |
| 4,820,277 A | 4/1989 | Norelli | |
| 4,822,343 A | 4/1989 | Beiser | |
| 4,904,244 A | 2/1990 | Harsh et al. | |
| 4,907,600 A * | 3/1990 | Spencer | A61B 5/15003 |
| | | | 600/577 |
| 4,984,580 A | 1/1991 | Wanamaker | |
| 5,201,716 A | 4/1993 | Richard | |
| 5,405,330 A | 4/1995 | Zunitch et al. | |
| 5,695,477 A | 12/1997 | Spikas | |
| 5,713,876 A | 2/1998 | Bogert et al. | |
| 5,775,673 A | 5/1998 | Kinsey | |
| 5,823,997 A | 10/1998 | Thorne | |
| 5,980,488 A | 11/1999 | Thorne | |
| RE37,908 E | 11/2002 | Kinsey | |
| D617,454 S | 6/2010 | Shaw | |
| 8,012,132 B2 | 9/2011 | Lum | |
| 2009/0270672 A1 | 10/2009 | Fago | |

FOREIGN PATENT DOCUMENTS

| | | |
|---|---|---|
| EP | 0747087 A2 | 12/1996 |
| EP | 0 787 501 A2 | 8/1997 |
| EP | 2879742 A1 | 6/2015 |
| EP | 3027250 B1 | 3/2017 |
| FR | 2645444 A1 | 10/1990 |
| FR | 2647351 A1 | 11/1990 |
| FR | 2733916 A1 | 11/1996 |
| GB | 2209470 A | 5/1989 |
| GB | 2518741 A | 4/2015 |
| JP | H01-120852 U | 8/1989 |
| JP | H01-179737 A | 7/1998 |
| JP | 2002 028246 A | 1/2002 |
| WO | 1990/000074 A1 | 1/1990 |
| WO | 90/00881 A1 | 2/1990 |
| WO | 90/11789 A1 | 10/1990 |
| WO | 1996/035466 A1 | 11/1996 |
| WO | 2006/045215 A1 | 5/2006 |
| WO | 2008/086004 A1 | 7/2008 |
| WO | 2011/159136 A1 | 12/2011 |
| WO | 2013/072182 A1 | 5/2013 |
| WO | 2013/164358 A1 | 11/2013 |
| WO | 2014/020090 A1 | 2/2014 |
| WO | 2015/014914 A1 | 2/2015 |

* cited by examiner

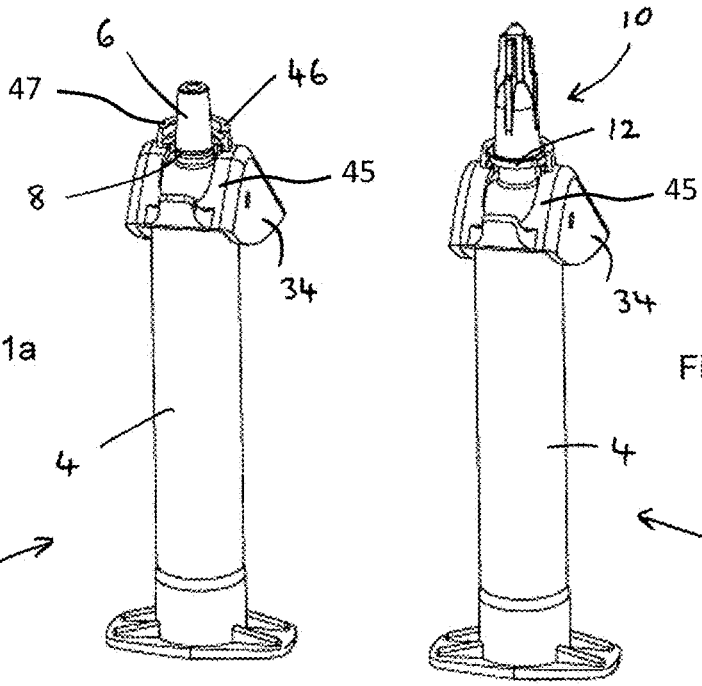
Figure 1a
Figure 1b
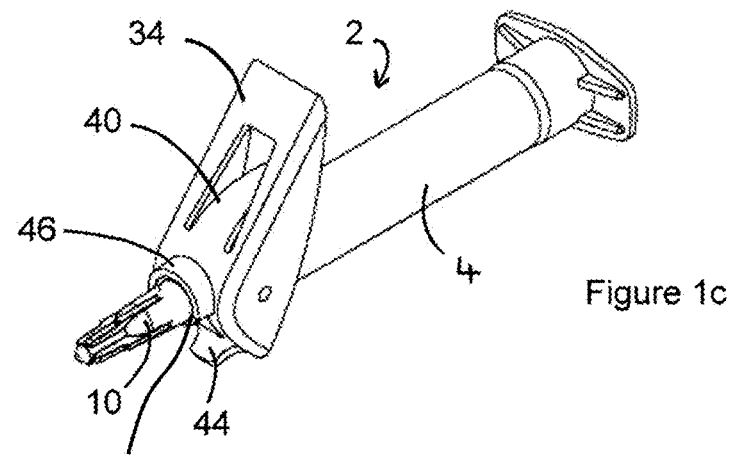
Figure 1c
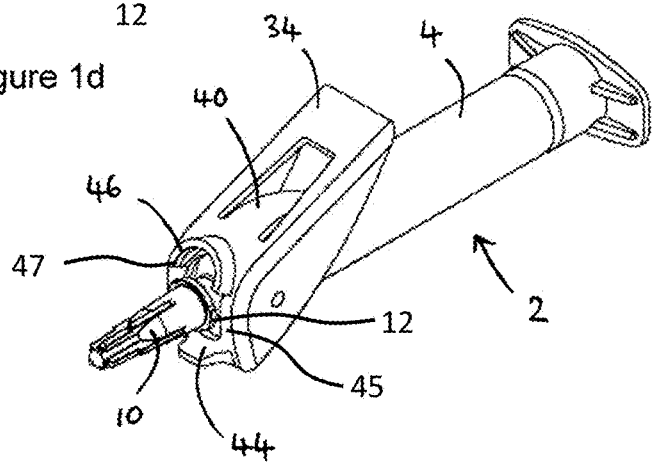
Figure 1d

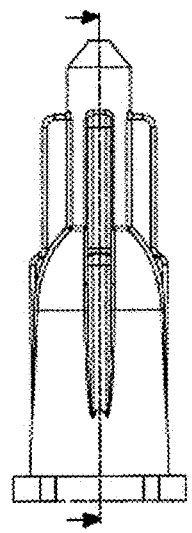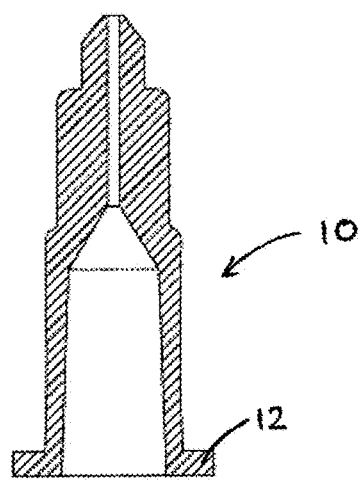
Fig. 2a Fig. 2b
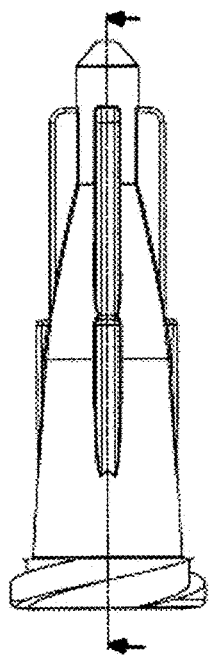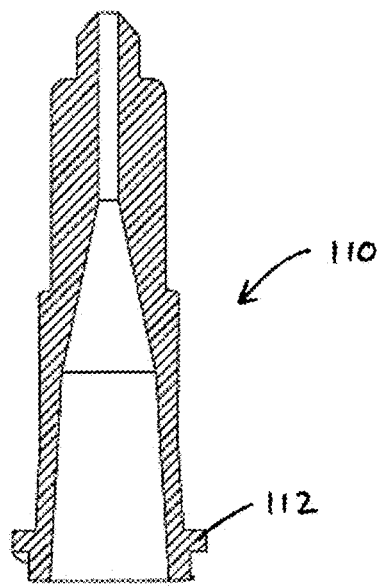
Fig. 3a Fig. 3b

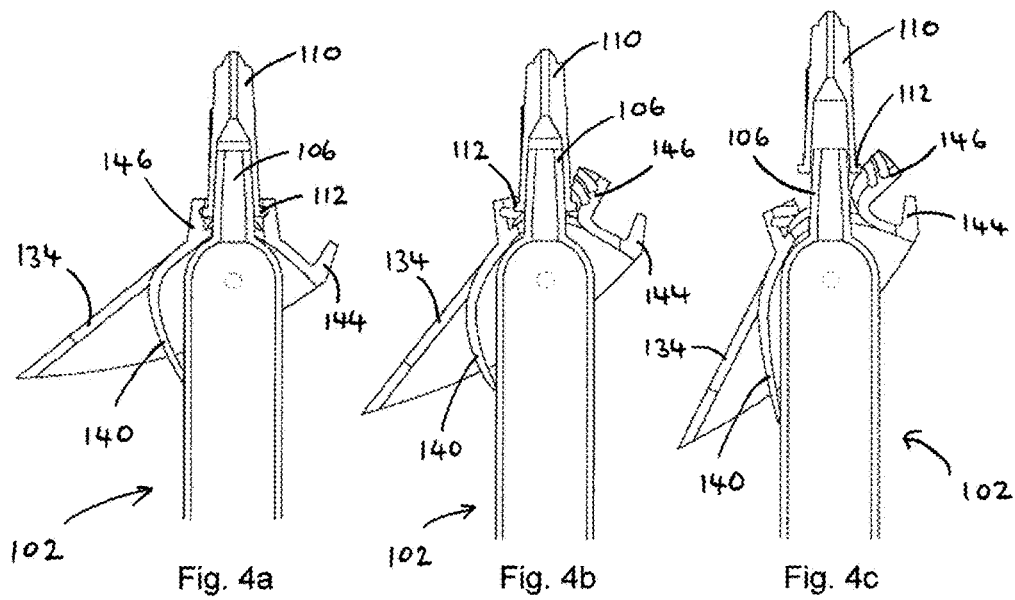
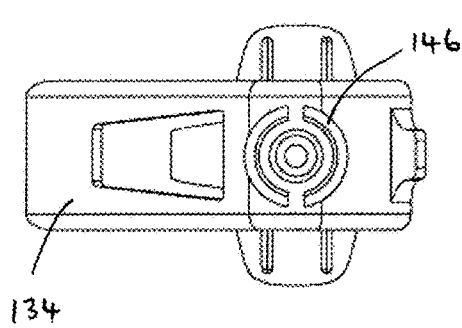 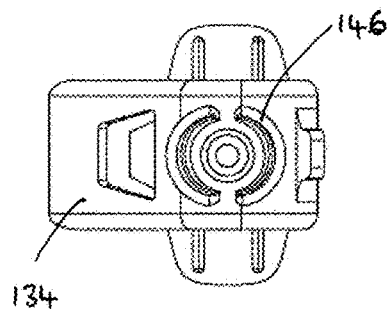
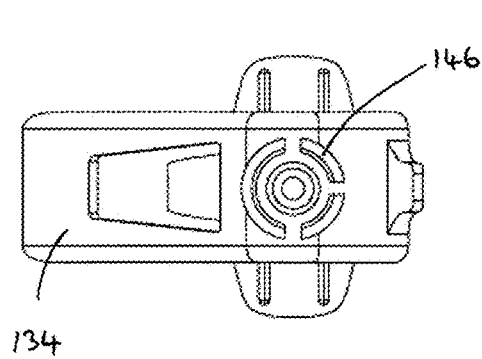 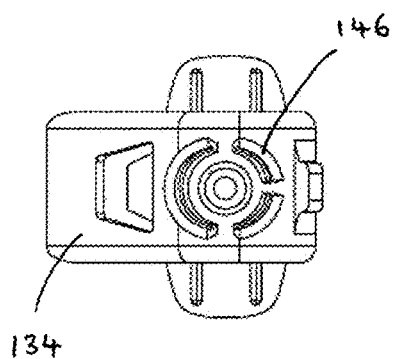

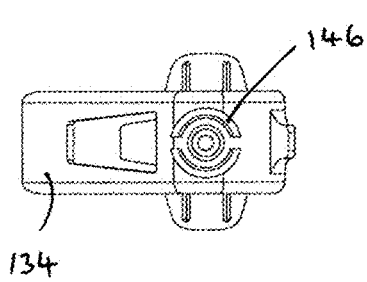
Fig. 8a
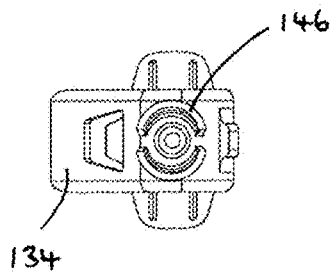
Fig. 8b
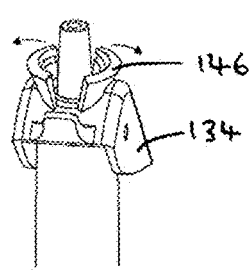
Fig. 8c

Fig. 9b 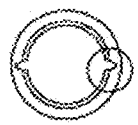 

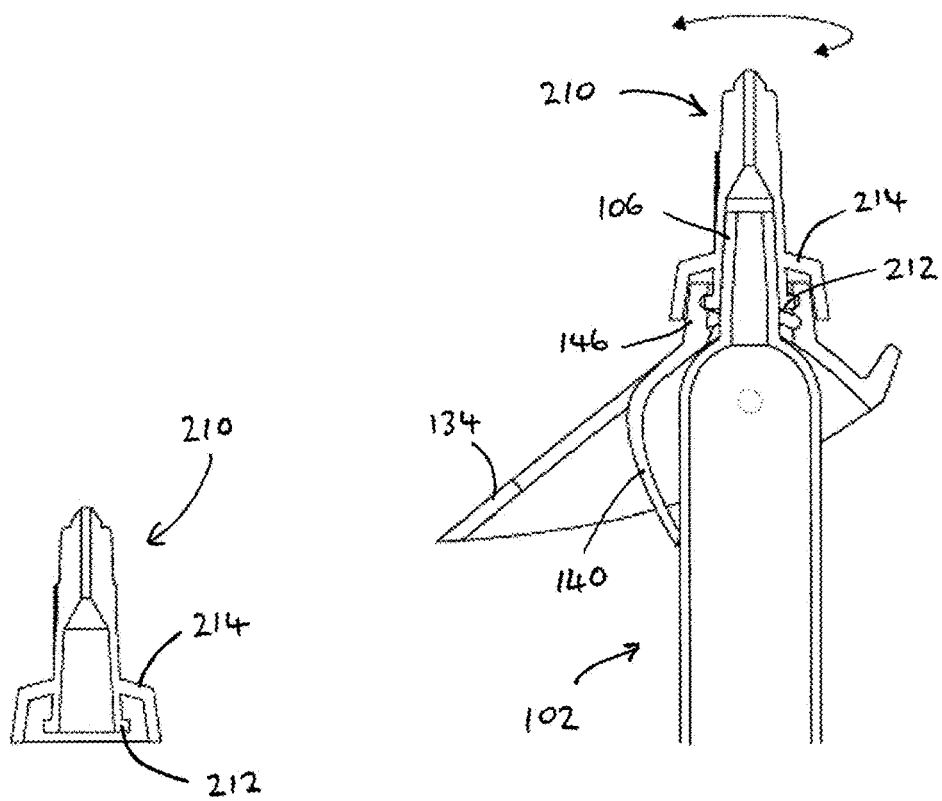
Fig. 12a
Fig. 12b
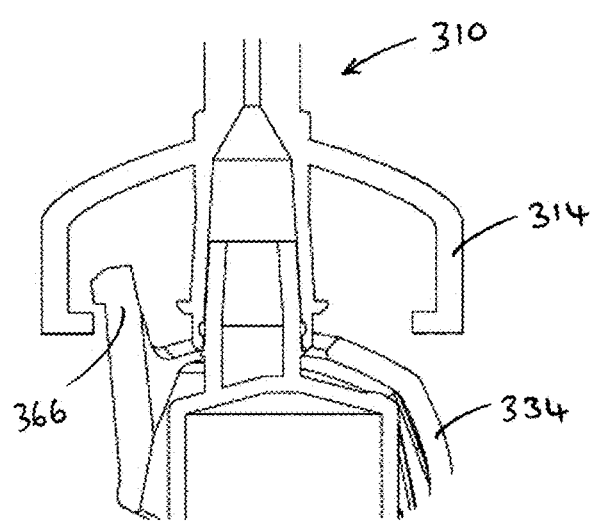
Fig. 13

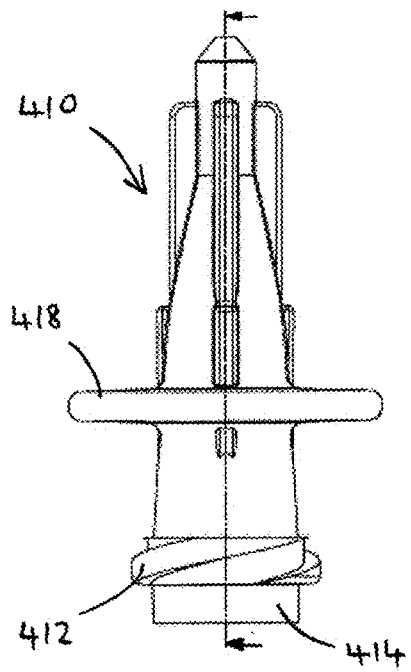
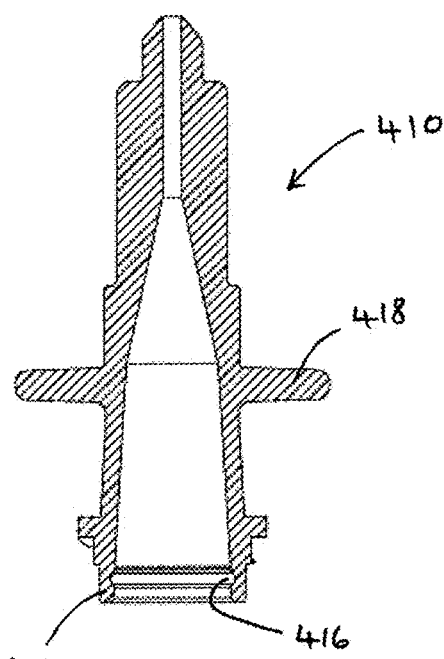
Fig. 14a    Fig. 14b
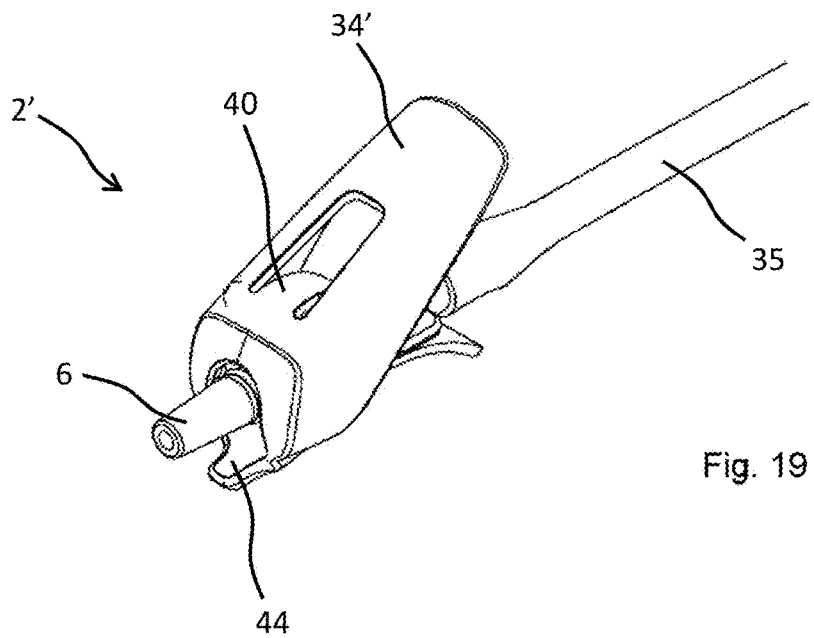
Fig. 19

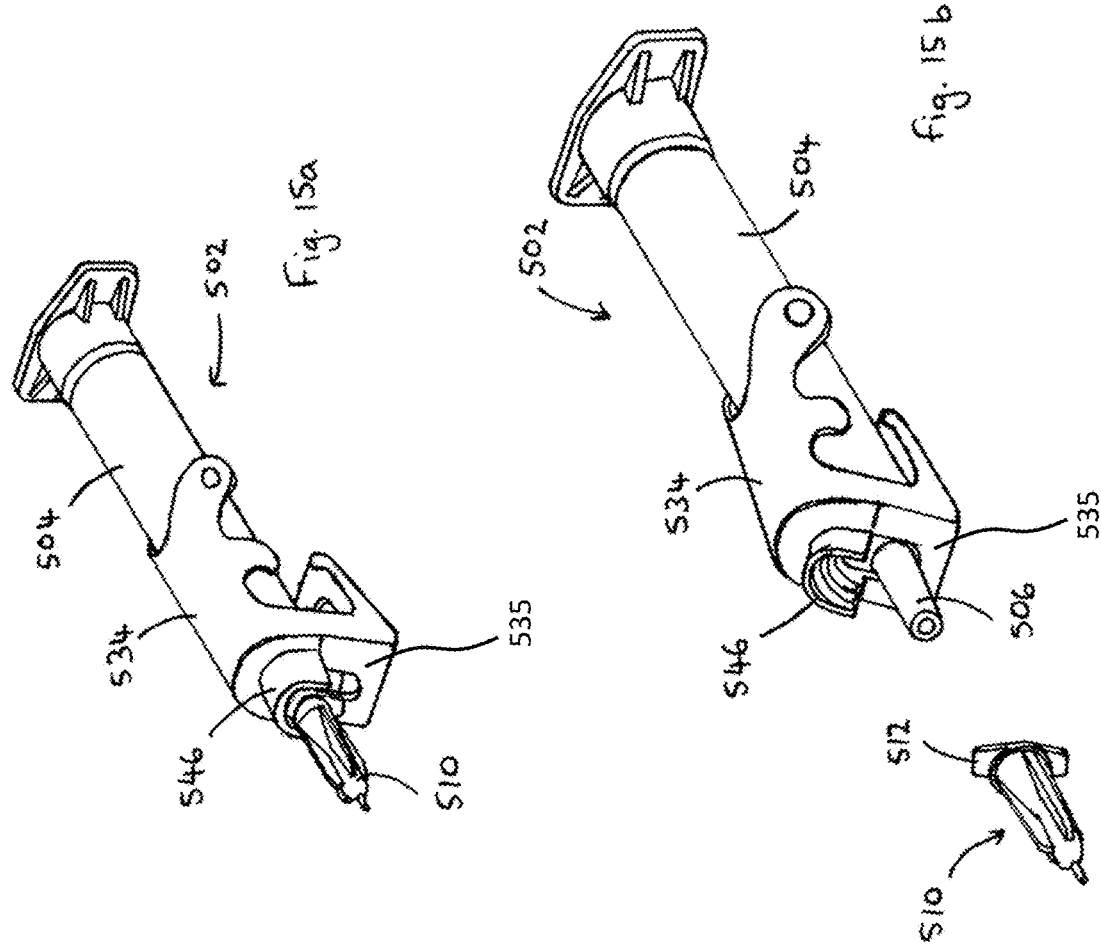

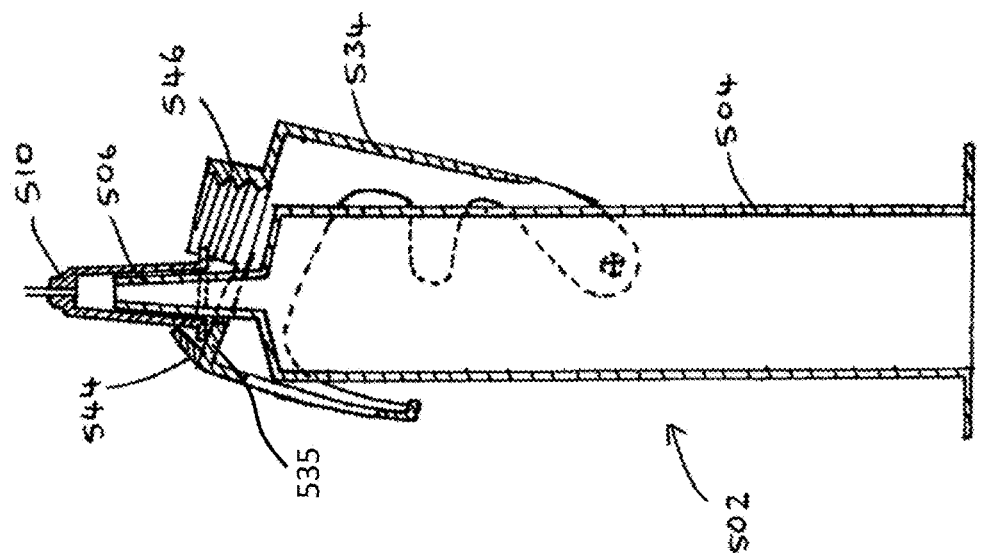
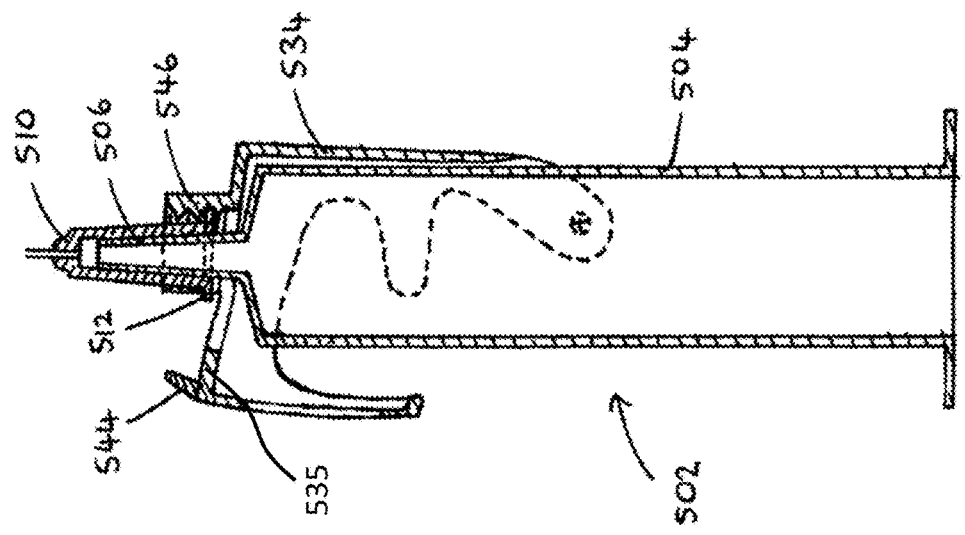

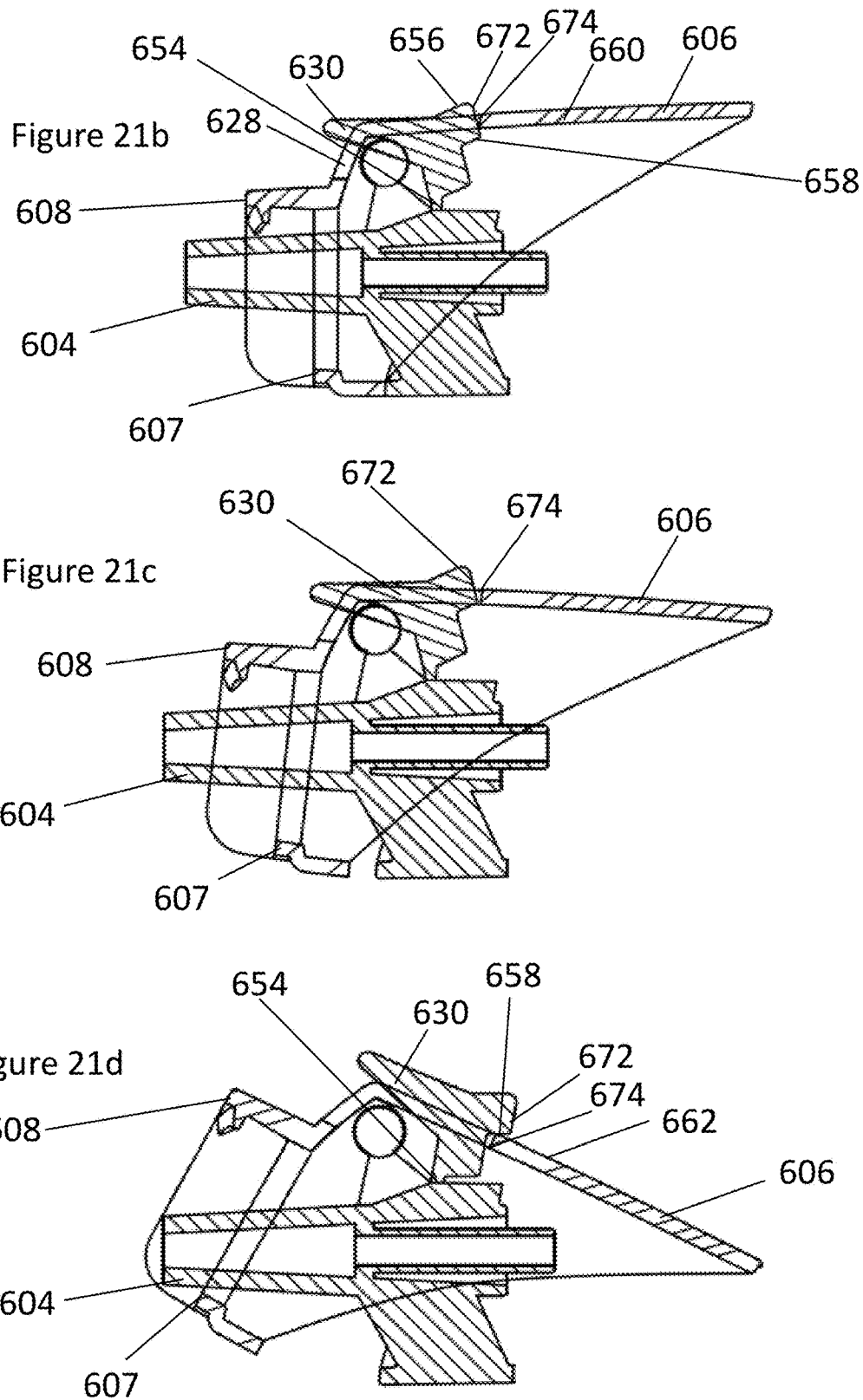

DISCONNECTING MECHANISMS

TECHNICAL FIELD

The present disclosure relates to the detachment of fluid-transferring devices and connections from a corresponding hub, and especially when transferring fluid in a medical setting. The disconnecting mechanisms, fluid transfer devices or fluid transfer connections as disclosed herein may find particular use in detaching a fluid transfer device such as a syringe, or other fluid transfer connection, from a hub that is connected to a living subject to/from whom fluid is being transferred.

BACKGROUND OF THE INVENTION

In a medical setting it may be necessary or desirable to transfer fluid to/from a subject for a variety of reasons. For example, a hub connected to a needle or other cannula may be used to draw blood from a vein or to infuse fluid substances i.e. intravenous (IV) therapy. A drip is one type of IV therapy. IV therapy may be used to correct electrolyte imbalances, to deliver medications or nutrition, for blood transfusion or as fluid replacement to correct dehydration. IV therapy can also be used for chemotherapy of cancer patients. Fluid-transferring devices such as syringes may also be attached to a hub that connects a cannula for the addition or removal of fluid to/from a variety of bodily cavities, organs or vessels. For instance, the hub may be part of an entity providing a catheter to drain urine from the bladder or kidney, to remove fluid from an abscess, to extract liquid from joints or cysts, or to administer breathing gases through a tracheal tube. A typical endotracheal tube includes a cuff inflation tube with a hub for attachment of a syringe to enable inflation to seal the trachea and bronchial tree against air leakage and aspiration of fluids. A tracheostomy tube or urinary tract catheter might also use a cuff system with a hub for connection of a syringe or other device to inject fluid to inflate a cup or balloon that holds it in place. However fluid injections using a syringe connected to a needle are one of the most common health care procedures in the world.

When transferring fluids to/from a subject, the hub with its needle, catheter or other cannula inserted in the patient is often left in-situ while the fluid-transferring device may be removed and replaced, e.g. to empty/re-fill a syringe or to change over the IV therapy. Where two medical devices that carry small fluid volumes must be connected, a standard Luer fitting is the most common means of achieving a leak-free junction. One type of Luer fitting, commonly called a "Luer lock/lok", uses an internally threaded collar surrounding a "Luer slip" friction fit (see below) tapered male tip of a syringe or the like. The projecting tip can be inserted into a corresponding female hub with an external thread and the collar screwed down to lock the connection. Such Luer lock fittings have the advantage of providing a secure connection that cannot easily come loose, but two hands are needed to hold the hub while screwing the device in/out. A more rapid form of attachment may be preferred in some circumstances, for example in an emergency situation. Another type of Luer fitting, commonly called a "Luer slip", simply uses a friction fit between a female hub and corresponding tapered male tip of a device without a threaded collar. A standard friction fit is achieved by a 6% taper. A Luer slip attachment is common for infusing less viscous fluids, such as vaccinations, and transferring fluids where high pressures are not involved, for example when drawing blood.

A problem observed with both Luer lock and Luer slip connections is the risk of injury when detaching the fluid-transferring device from a hub that is still connected to a patient. While a medical practitioner might take care to hold the hub and avoid injury when unscrewing a Luer lock connection, there is a temptation with a Luer slip connection to try to pull the device from the hub e.g. with one hand. However this can easily result in the hub being tugged away from the body and causing tissue damage. Often the device may not be pulled in a straight line with the cannula connected to the hub, but rotated, and this can twist the components. The tape used to hold the hub e.g. IV port in position is often loosened from the skin and its cannula e.g. needle may even be accidentally extracted. When emptying fluid from a body cavity, for example, keeping the needle hub still when detaching the syringe can be essential to avoid diffuse cutting inside the cavity or damage of the cavity wall. In addition there is a risk of unacknowledged contamination of both the hub and the Luer tip (not only the user) when holding the very small hub with the thumb and index fingers while pulling away the male tip, the tip sliding past the user's fingers as it is released.

Moreover tugging with a single hand does not usually apply enough force even to pull the device out of a friction fitting (such as a Luer slip) and, depending on the force used when connecting the Luer slip tip to the hub, the practitioner usually needs to hold or push the hub while also pulling the device so that it becomes detached. Typically the device will be rotated simultaneously while pulling away from the hub. This jerking can result in unwanted extraction of the needle or other component connected to the hub. The connection will often be pressurised by fluid. For example, a cuff connected to a tracheostomy tube, endotracheal tube or urinary catheter often has a tight connection of the male Luer tip with two-handed operation being required to loosen the connection while the sprung piston in the female Luer hub blocks the outflow of fluid (air or liquid) from the cuff.

Ease of disconnection can be a problem not only when detaching a device from a hub connected to a patient but also when it is desired to fill/empty a device such as a syringe via a fluid hub in a quick and convenient manner. For example, when filling a syringe using a needle inserted in a vial, each time that the syringe is removed it requires two hands to firmly grasp the needle hub and the syringe to separate them while the needle remains in the vial. As mentioned above, there is again a risk of contamination as the user grasps the hub and the tip comes into contact with the fingers holding the hub.

Another situation where a user might come into contact with a needle hub is when using a blood collection tube. The blood tubes are evacuated plastic or glass containers sealed with an elastomeric septum that is pierceable by a double-ended needle to draw venous blood. Due to the piercing force and pressure differential, a secure connection to the needle assembly is required and therefore a threaded Luer lock connection is normally used rather than a Luer slip. U.S. Pat. No. 5,201,716 proposes an alternative blood specimen collection system that does not require the needle assembly to be grasped and twisted during disconnection. In this system a needle assembly is mounted with an interference fit rather than a threaded connection. A pivotally mounted lever assembly is spring-biased to hold the needle assembly in position, i.e. to provide an additional level of security over the friction fit. If the lever is actuated against its spring bias then there is only an interference fit holding the needle assembly in place. The lever can be pivoted to simultaneously release the spring bias and to apply a forward ejection force to the needle assembly.

In any situation where one hand is holding a needle hub while pulling a device away there is a risk of needlestick injury and contamination. Needle caps frequently being mislaid or forgotten can exacerbate this. This also applies when separating a needle or other contaminated component from a syringe or similar device for disposal purposes, with many needlestick injuries occurring when trying to remove sharps to throw into a bin. Usually the person handling a syringe will try to cover a contaminated needle with a cap after use, before grasping the hub to separate the needle from the syringe barrel for disposal. However, when mounting a needle cap onto the contaminated needle a person will use the large muscle groups in the arms and shoulders that work less precisely and, combined with poor depth of vision, this often results in a needlestick injury to the fingers holding the needle cap. It would be better if a needle hub could be safely released without needing to cap the needle or handle the connection.

There are various fluid transfer procedures in the medical setting that may require a very secure connection between a fluid transfer tip (e.g. provided by a syringe) and a corresponding hub. The hub may be connected to a needle or catheter inserted into an artery, vein, cavity or organ of a patient. In the field of cardiology, angiography and angioplasty procedures may inject fluids (liquid and/or air) into narrow channels at high pressure. Manual syringes and manifold sets are used for percutaneous coronary interventions and coronary diagnostic procedures such as angiography. A cardiac angiographic kit typically comprises a catheter hub for connection, a catheter body of chosen size, length and stiffness, and a tip with a single end-hole to eject fluids. The catheter body is inserted into the coronary vessels, ventricles and/or peripheral vasculature. A syringe may be connected to the catheter hub to inject contrast agents or saline at pressures ranging between 250 and 800 psi, and even up to 1000 or 1200 psi (84 bar). The catheter hub has an external thread to provide a standard Luer lock connection.

Luer lock connectors have become universal, not only for joining syringes to hubs, but also for connecting small-bore medical tubing and hoses for liquids and/or gases. Luer lock connections are commonly used for vascular IV lines but also find use in other medical treatment or diagnostic systems. Tubing and hoses may use a Luer lock connection for cuff inflation systems, feeding tubes, catheters, and hoses for vascular, enteral, respiratory, neuraxial and urethral/urinary systems.

The screw connection of a Luer lock hub is often considered necessary to withstand high pressures. However a syringe, hose or other fluid transfer device must be rotated to connect, and disconnect, its Luer lock collar to/from the hub. This can take time and requires a two-handed operation. Furthermore, when a user grips the hub to unscrew the connection there is a risk of contamination, especially where the hub includes a needle that may carry blood on its shaft. It would improve the efficiency and workflow of medical procedures if a fluid transfer device could be disconnected from a Luer lock hub more easily.

The universal Luer-type connectors with 6% taper, i.e. conforming to ISO 80369-7, have been used for decades in all kinds of fluid transfer devices and connections in medical procedures. More recently, there has been a drive to introduce non-Luer connectors for devices used for neuraxial (e.g. intrathecal and epidural) procedures and peripheral nerve anaesthesia blocks to avoid the accidental, but potentially fatal, connection of an intravenous infusion or injection. The International Standard ISO 80369 now includes a dedicated connector type for neuraxial applications, known as NRFit® (ISO 80369-6), that is not compatible with Luer connectors. Furthermore, ISO 80369 also includes a dedicated connector type for enteral applications, known as ENFit (ISO 80369-3), that is again incompatible with Luer connectors e.g. to prevent feeding tubes being erroneously connected to IV tubing. ISO 80369 specifies dimensions and requirements for the design and functional performance of these small-bore connectors intended to be used with medical devices. However, it is a common feature of all small bore connectors for fluids in healthcare applications to include a tapered fluid transfer tip. Luer lock, NRFit® and ENFit connector parts all comprise a tapered male connector tip surrounded by a coaxial connection collar having an internally threaded annular surface. The issues described above in relation to Luer lock connections apply equally when disconnecting NRFit® or ENFit connector parts.

The present disclosure seeks to address or mitigate the problems outlined above.

SUMMARY OF THE INVENTION

There is disclosed a fluid transfer device comprising: a fluid transfer tip, the fluid transfer tip comprising a tapered friction fitting for a corresponding hub; a lever member pivotally mounted to move relative to the fluid transfer tip; and a screw thread mounted on the lever member to enable a hub to be connected to the tip by a screw fit in addition to the friction fitting; wherein the lever member is resiliently biased so that the screw thread is positioned to form a screw fit with the hub; and wherein the hub can be disconnected by pivoting the lever member against the resilient bias to release the screw fit with the hub and to subsequently release the hub from the friction fitting.

Such a device provides a novel mechanism for locking with a screw fit and automatic release using a lever. The screw thread mounted on the lever member enables a hub carrying a screw thread, such as a standard Luer lock hub, to be connected to the device. The hub may be connected by relative rotation, as is conventional, to ensure a tight screw connection. Such a Luer lock connection may be suited to high pressure fluid transfer procedures. A benefit of the operating the lever member to pivot away the screw thread and release the screw fit is that a hub can be disconnected from the device without an unscrewing action. The usual two-handed operation of unscrewed can be replaced by a simple one-handed operation of the lever member. Such a device may furthermore be connected to a hub carrying a flange, such as a standard Luer slip hub, with the screw thread engaging the flange to provide a positive connection in addition to the friction fitting. Other hub designs may also be positively engaged by the screw thread, as is explained further below.

The screw thread mounted on the lever member can be considered a kind of latch, as pivoting the lever member against the resilient bias releases the latch so that the screw thread is separated from a corresponding thread on an outer surface of the connected hub. This leaves the hub connected by the friction fitting alone. Simply releasing the screw fit is not enough to disconnect the hub from the fluid transfer tip; the hub cannot fall away from the tip under gravity due to the friction fitting. The lever member has the additional function of also releasing the hub from the friction fitting.

This can be achieved in a single smooth action by the lever member, for example a front surface thereof, moving relative to the fluid transfer tip to push away the hub and release the friction fitting. In a preferred set of embodiments the a lever member is pivotally connected to the device with one end, such as a front surface, moveable between first and second positions relative to the fluid transfer tip.

The lever member is resiliently biased so that the screw thread is positioned to form a screw fit with the hub. This means that the default position of the lever member is one that maintains a Luer lock connection. This ensures safety and reliability. A user must actively overcome the resilient bias to release the screw fit with the hub.

As is mentioned above, a hub may be connected to the screw thread by rotating the hub as it is pushed onto the fluid transfer tip. The lever member may remain in its resiliently biased position while the hub is being connected in this way. For example, a standard Luer lock hub may be rotated by up to 270° to ensure connection of its outer screw thread with the screw thread mounted on the lever member. However, the Applicant has recognised that the time and/or manual dexterity required to rotate a hub to form the screw fit may not always be desirable. The resilient bias of the lever member means that is can be pushed aside to enable faster connection of a hub. This provides an improvement over standard Luer lock connections. For example, a hub may be pushed onto the fluid transfer tip without rotation, forcing the lever member to pivot against its resilient bias so that the screw thread is not engaged while the hub is connected onto the tapered friction fitting. A final, short rotation of the hub may then allow the screw thread to engage and the lever to return to its resiliently biased position. This may only require a turn through 90° (or less), rather than 180° or 270°, to complete the screw fit connection. The screw thread may only be partially threaded.

The screw thread mounted on the lever member may take the form of a standard helical thread. The cross-sectional shape of the thread (often called its form or thread form) may be square, rectangular, triangular (e.g. V-shaped), trapezoidal, or other shapes. A standard triangular thread form is based on an isosceles triangle and usually called V-threads. An equilateral triangle provides 60° V-threads. However it is envisaged that the screw thread may have a thread form that assists a hub in being pushed onto the tip without requiring full rotation. The screw thread may have a non-equilateral triangular thread form. For example, a triangular thread form may be angle downwardly, along a direction of decreasing taper of the fluid transfer tip, to assist in a hub pushing past the screw thread and then engaging the screw fit once the friction fitting has been formed. The thread form may even include downwardly extending teeth, or other gripping means, that prevent a hub from being forcibly disconnected without pivoting the lever member to release the screw fit. Various different thread forms may be considered, especially where the device is intended to be connected to a hub that does not carry a standard Luer lock threaded collar, e.g. a Luer slip hub carrying a flange, or any other kind of hub that can form a friction fitting with the tapered fluid transfer tip.

An advantage of using a lever member to disconnect the tip from a corresponding hub is that it can amplify an input force to provide a greater output force, i.e. providing leverage to push a hub away from the tip. The mechanical advantage of a lever member can increase the force applied so that the device can be released without necessarily holding the hub, thereby enabling single-handed operation. Furthermore, a lever member can be ideally suited to engage the screw fit when pivoted under the resilient bias and to move the hub out of the screw fit as it pivots against the resilient bias, with further pivotal movement of the lever member also acting to release the hub from the friction fitting.

In a set of embodiments the screw thread is an internal thread carried by a partial circular or semicircular collar. As such a collar only extends around one side of the fluid transfer tip, e.g. up to 180° around the circumference of the fluid transfer tip, the screw fit may be released simply by pivoting the lever member to move the collar away from the fluid transfer tip and hub connected thereto.

More generally, it is preferable that the screw thread mounted on the lever member takes the form of an internally threaded collar. Such a collar may be mounted on the lever member to at least partially surround the fluid transfer tip. In order to ensure a secure Luer lock connection, the internally threaded collar may extend substantially 360° around the circumference of the fluid transfer tip. However a 360° collar can make it more difficult for the lever member to operate to release the screw fit, as the collar must be moved away from the fluid transfer tip on all sides. The Applicant has devised a solution wherein the internally threaded collar is separable into multiple segments that are arranged to be moved apart by pivoting the lever member against the resilient bias, thereby releasing the screw fit with the hub.

This solution applies, regardless of whether the lever member is resiliently biased, and not only for fluid transfer devices (such as syringes) but any fluid transfer connection in general. Thus there is disclosed a fluid transfer connection comprising: a fluid transfer tip comprising a tapered friction fitting for a corresponding hub; a lever member pivotally mounted to move relative to the fluid transfer tip; and an internally threaded collar mounted on the lever member to at least partially surround the fluid transfer tip and enable a hub to be connected to the tip by a screw fit in addition to the friction fitting; wherein the internally threaded collar is separable into multiple segments; and wherein a hub is disconnected by pivoting the lever member to move the segments apart and thereby release the screw fit.

Such a fluid transfer connection benefits from the screw fit of a standard Luer lock connection, which is trusted to withstand pressurised fluid transfer procedures, but enables the Luer lock connection to be released by operating the lever member instead of unscrewing the tip from a corresponding hub. This can be a simple one-handed gesture rather than a two-handed twisting movement. The separable collar allows the lever-operated disconnection mechanism to cooperate with a standard Luer lock hub.

The internally threaded collar may be separable into multiple segments that are arranged around the circumference of the fluid transfer tip, for example partially circular or semicircular e.g. arcuate segments. The multiple segments may move apart, for example by moving radially, in a direction that is in line with lever member or orthogonal to the lever member. Preferably at least some of the segments move radially outwardly relative to the fluid transfer tip. It will be appreciated that not all of the segments necessarily move radially outwardly relative to the fluid transfer tip. For example, one or more of the segments may stay still while one or more other segments move outwardly to result in the segments being spaced apart.

The internally threaded collar may surround the fluid transfer tip by up to 360°, in continuous or spaced segments. A secure Luer lock connection may be achieved by a collar that extends at least 180°, 190°, 200°, 210°, 220°, 230°, 240°, 250°, 260°, 270°, 280°, 290°, 300°, 310°, 320°, 330°, 340°, or 350° around the circumference of the fluid transfer tip. In preferred embodiments the internally threaded collar extends substantially 360° around the circumference of the fluid transfer tip. The movable segments of the collar enable a 360° screw fit to be achieved which is conveniently released by operating the lever member.

According to at least some embodiments the lever member may be freely pivotable, allowing a user to easily open and close the collar to connect and disconnect a hub as desired. However it may be preferable that the lever member has a default position that holds the collar closed to form the screw fit. In a preferred set of embodiments the lever member is resiliently biased so that the internally threaded collar surrounds the fluid transfer tip to form a screw fit with the hub. A user must therefore operate the lever member with sufficient force to overcome the resilient bias before the screw fit is released. This can prevent the Luer lock connection from being accidentally released. It is therefore preferable that the segments are only moved apart by pivoting the lever member against the resilient bias.

The lever member may act to separate the internally threaded collar into multiple segments that are already defined e.g. formed during manufacture. In one set of embodiments the internally threaded collar comprises pre-separated multiple segments. However the force applied by the lever member may instead be exploited to physically separate the collar into segments, for example breaking open frangible connections or areas of weakness formed in the collar. In another set of embodiments the internally threaded collar is arranged to be broken into multiple segments.

The fluid transfer tip may be connected and reconnected to a hub more than once. In a set of embodiments the internally threaded collar may be separable into hinged segments. Such hinged segments may be opened and closed by operation of the lever member. However, in at least some embodiments it is preferable that the fluid transfer tip can only be used once, e.g. to prevent cross-contamination. The collar may be designed to undergo permanent damage during disconnection of a hub so that the fluid transfer connection or device cannot be re-used. In a set of embodiments there may be provided means for locking the multiple segments apart.

In some embodiments, operation of the lever member may leave a hub connected to the tip by the friction fitting. Manual intervention may be required to fully disconnect the hub, for example a user may need to pull away the hub. However the friction fitting may not be easy to release manually, and a twisting action might be requires to loosen the hub. It is therefore preferable that pivoting the lever member subsequently releases the hub from the friction fitting. As is mentioned above, the lever member, for example a front surface thereof, can be arranged to move relative to the fluid transfer tip to push away the hub and release the friction fitting. In a set of embodiments the lever member comprises a front surface having a rim arranged to move forwards along the tip after the segments have been moved apart.

The Applicant has further recognised that a resilient bias may not be an essential feature to at least some further aspects of the disclosure. Thus there is disclosed a fluid transfer device or connection comprising: a fluid transfer tip, the fluid transfer tip comprising a tapered friction fitting for a corresponding hub; a lever member pivotally mounted to move relative to the fluid transfer tip; and a screw thread mounted on the lever member to enable a hub to be connected to the tip by a screw fit in addition to the friction fitting; wherein the lever member is operable to move the screw thread between at least two different positions, wherein in a first position the screw thread engages the hub and thereby assists in holding the hub in a locked position and in a second position the screw thread does not engage the hub and the lever member acts to release the hub from the friction fitting.

It is preferable that the lever member is manually operable to pivot between the first and second positions. A resilient bias may optionally be used to assist manual operation. For example, the lever member may be resiliently biased to move the screw thread into the first position. This can ensure that the screw thread automatically engages the tip without manual intervention, i.e. the locking position is the default position. Manual operation of the lever member can then overcome the bias force to move the screw thread from the first position to the second position when it is desired to release the screw fit and then disconnect the friction fitting, e.g. by pushing away the hub. However, in some embodiments the presence of such a resilient bias, e.g. a spring member, may require a user to actively operate the lever member when it is desired to connect a hub to the fluid transfer tip, whereas without a resilient bias the lever member can be left in the second position (or a neutral third position) where the screw thread is moved out of the way.

In at least one set of embodiments, the lever member is preferably mounted so as to freely pivot between the first and second positions. This removes the need for a user to overcome a bias force and can make it easier to control the lever member. This may provide a user with manual dexterity in controlling movement of the lever member and selective connection/disconnection of a hub.

Even without a resilient bias, e.g. a spring member, the lever member may be arranged so as to hold the screw thread in the first position. Thus alternatively, or in addition to a resilient bias, the lever member may hold itself in the first position or the fluid transfer device/connection may act to hold the lever member in the first position. For example, the fluid transfer device may comprise a fluid chamber connected to the fluid transfer tip (e.g. a syringe) and the lever member may grip onto the fluid chamber when it moves to the first position. A user may need to apply a force to overcome the grip before the lever member can be moved away from the first position. Thus in a set of embodiments the fluid transfer device or connection further comprises gripping means arranged to hold the lever member in the first position. Such gripping means act in addition to the screw fit or other positive connection to the hub.

As mentioned above, in a set of embodiments the lever member may be operable to move the screw thread into a third position, between the first and second positions, where the screw thread no longer holds the hub in a locked position but allows the hub to remain connected to the fluid transfer tip by the friction fitting.

The lever member may comprise an actuator portion, e.g. provided by a front surface, that acts to release the hub from the friction fitting. The actuator portion is preferably arranged to move along the tip when the lever member is pivoted between the different positions. Such embodiments are described further below.

According to an aspect of the present invention there is provided a fluid transfer device or fluid transfer connection comprising:

a fluid transfer tip, the fluid transfer tip comprising a tapered friction fitting for a corresponding hub;

a lever member pivotally mounted to move relative to the fluid transfer tip; and a screw thread mounted on the lever member to enable a hub to be connected to the tip by a screw fit in addition to the friction fitting;

wherein the lever member is operable to move the screw thread between at least two different positions, wherein in a first position the screw thread engages the hub and in a second position the screw thread does not engage the hub and the lever member acts to release the hub from the friction fitting, and wherein the lever member is held with the screw thread in the first position and thereby assists in holding the hub in a locked position.

As the lever member is arranged to hold the screw thread in the first position, when a hub is connected to the tip this assists in holding the hub in a locked position. The lever member must be actively moved out of its hold before being operated to move the screw thread between the at least two different positions. This can prevent accidental disconnection, for example during use of the fluid transfer device or connection. This may be particularly beneficial if a subject has an IV line in position and there is a risk of the fluid transfer device or connection being knocked by the subject's movements e.g. rolling over in bed. In at least some embodiments the fluid transfer device or fluid transfer connection may further comprise a hose or tubing in fluid connection with the fluid transfer tip. In use, there may be a hub or Luer part connected to the fluid transfer tip by the tapered friction fitting and by a positive connection between the screw thread and an outer rim or outer thread at a base of the hub.

In order for the lever member to hold the screw thread in the first position, the device or connection may further comprise a locking arrangement for the lever member. Preferably the lever member is held with the screw thread in the first position by the locking arrangement. In embodiments wherein the lever member is resiliently biased to move the screw thread into the first position, the lever member may be locked against the resilient bias by the locking arrangement. In addition, or alternatively, the lever member may be held in the second position, against the resilient bias, by the locking arrangement. In various embodiments, the locking arrangement comprises a locking member moveable to engage with the lever member and prevent the lever member from pivoting. Preferably the locking member is moveable by a user to actively unlock the lever member so that it can be pivoted.

In various embodiments, the fluid transfer device or connection comprises a main body including the fluid transfer tip, wherein the lever member is pivotally mounted to the main body. In such embodiments the main body may further include a fluid transfer passage in fluid communication with the fluid transfer tip. For example, the fluid transfer tip and the fluid transfer passage may be integral parts of the main body. The fluid transfer passage may be arranged for connection with an external fluid transfer hose or tubing.

Any of the embodiments described herein may take the form of a lever-actuated disconnection mechanism mounted to a fluid transfer tip at the end of a fluid transfer hose.

According to a further aspect of the present invention there is provided a disconnecting mechanism comprising:
a main body including:
a fluid transfer tip having a tapered surface to form a friction fit with a corresponding connector part; and
a fluid transfer passage in fluid communication with the fluid transfer tip and passing through the main body; and
a lever member pivotally mounted to the main body, the lever member including:

a threaded portion projecting from the lever member to enable the corresponding connector part to be connected to the fluid transfer tip by a screw fit in addition to the friction fit; and
an actuator portion provided by a front surface of the lever member to actuate release of the friction fit;
wherein, in a first pivotal position of the lever member, the threaded portion has a first position close to the fluid transfer tip to engage with an outer thread or rim of the corresponding connector part connected onto the fluid transfer tip and thereby form the screw fit in addition to the friction fit and, in a second pivotal position of the lever member, the threaded portion has a second position further away from the fluid transfer tip than the first position to disconnect the screw fit and the actuator portion is moved forwards along the fluid transfer tip to push away the corresponding connector part and thereby actuate release of the friction fit.

Such a disconnecting mechanism functions in the same way as previously described, with the lever member pivoting so as to cause the screw fit to be disconnected and the friction fit to be released. These two actions may occur at least partially simultaneously, or as two distinct actions in time.

In one or more embodiments, the disconnecting mechanism further comprises a locking mechanism arranged between the main body and the lever member to prevent the lever member from moving out of the first pivotal position. In one or more embodiments, the locking mechanism is further arranged to prevent the lever member from moving out of the second pivotal position. In one or more embodiments, the locking mechanism comprises a first locking surface that is engaged with the lever member when in the first pivotal position. In one or more embodiments, the first locking surface is part of a locking member that is manually moveable to disengage the first locking surface from the lever member and allow the lever member to move out of the first pivotal position. In one or more embodiments, the locking mechanism comprises a second locking surface that is engaged with the lever member when in the second pivotal position. In one or more embodiments, the second locking surface is part of the same locking member, or another locking member, that is manually moveable to disengage the second locking surface from the lever member and allow the lever member to move out of the second pivotal position.

The lever member of the disconnecting mechanism may be structured as follows. Preferably the threaded portion projects forwards from the front surface of the lever member such that, in the first pivotal position of the lever member, the threaded portion is further forward along the fluid transfer tip than the actuator portion. This means that, ideally, the screw fit is connected without the actuator portion being in contact with the corresponding connector part. In addition, or alternatively, the threaded portion is preferably an internally threaded collar arranged such that, in the first pivotal position of the lever member, the collar surrounds the fluid transfer tip by up to 180°. This helps to ensure the security of the screw fit, whether the threaded portion engages with an outer thread or rim of a corresponding connector part.

In one or more embodiments, the fluid transfer tip and the fluid transfer passage may be integral parts of the main body. In one or more embodiments, the disconnecting mechanism further comprises a hose or flexible tubing connected to the fluid transfer passage. In some embodiments the hose or tubing may be fixed to the main body, e.g. a welded connection with the fluid transfer passage. In some embodiments the hose or tubing may be removably connected to the fluid transfer passage.

While the lever member may take many different forms, preferably the lever member comprises a front surface that is substantially transverse to the axis of the tip and the front surface is arranged to move along the tip when the lever member is pivoted against the resilient bias. In order for the lever member to transfer force efficiently, it is preferable for it to be relatively stiff. However it may also be desirable to mould the device, or at least the lever member, from plastics materials so as to provide a cheap, sterile and disposable product for single use in a medical setting. The lever member may be stiffened by forming it as a three-dimensional shell. Preferably the lever member comprises a front surface that is substantially transverse to the axis of the tip and one or more side surfaces that extend in a direction substantially parallel to the axis of the tip. Preferably the surfaces form a shroud extending back from the front surface and away from the fluid transfer tip. The three-dimensional extent of the member can help to ensure that it is stiff even if formed of a plastics material, as is preferred in various embodiments.

In a set of embodiments the lever member has an at least partially cylindrical form with the side surface(s) extending substantially parallel to the axis of the fluid transfer tip being cylindrical side surfaces. The side surface(s) do not need to fully surround the axis of the fluid transfer tip. But in at least one set of embodiments the front surface of the lever member is connected to one or more side surfaces that surround the fluid transfer tip. This can stiffen the lever member so that the front surface preferably does not flex when pushed against a hub but instead transmits its kinetic energy to move the hub away.

Alternatively, or in addition, the front and side surface(s) of the lever member are preferably integrally formed. For example, at least these parts of the lever member may be formed as a single plastics moulding. Alternatively, or in addition, it is preferable that the front surface at least partially surrounds the fluid transfer tip. The front surface may entirely surround the fluid transfer tip, for example with the tip protruding through an aperture in the front surface. This can make the lever member more compact and/or make the front surface more effective in pushing against a hub mounted on the fluid transfer tip with a friction fit.

A further advantage of using a lever member to disconnect the hub is that the shape, in particular the curvature, of the front surface can be designed to control the leverage that is achieved. In one set of embodiments the front surface is curved such that initial movement of the lever member (e.g. against a resilient bias) moves the front surface substantially transverse to the fluid transfer tip to release engagement of the screw fit and further movement of the lever member (e.g. against the resilient bias) moves the front surface along the fluid transfer tip to release the hub from the friction fitting. Accordingly the curvature of the front surface provides for two different movements that are matched to the different stages of disconnection.

A potential problem with pushing a hub away from a tip is that it may be forcibly disconnected. If the hub is carrying a needle or other sharp object then this could pose an injury risk. It is therefore preferable that the device further comprises a catch means arranged to catch the hub after it has been released from the friction fitting. Preferably further movement of the lever member (e.g. against a resilient bias) causes the catch means to catch the hub. In this way the hub may be caught as it becomes disconnected but then controllably separated from the device. The catch means be may be subsequently released by resiliently biased movement of the lever member, e.g. back to its resting state.

It may be desirable to disable the resilient bias (where provided) when the device is not in use, for example to make it compact for storage and/or transport. A generally applicable feature is for the device to comprise means to lock the lever member against the resilient bias.

In any of the embodiments described above, the fluid transfer device or connection may include means for mounting the lever member. Where the lever member comprises one or more side surfaces that extend in a direction substantially parallel to the axis of the fluid transfer tip, for example in a cylindrical or rectangular form, the side surface(s) can conveniently extend along at least part of the device to engage with such mounting means. Accordingly the fluid transfer device or connection can be conveniently provided with the lever member mounted ready for assistance in disconnecting the tip from a hub during use. At least some embodiments may therefore provide a new category of fluid transfer devices, such as syringes, or other fluid transfer connections, that are manufactured and/or sold with a lever member pre-mounted ready for use. While the lever member could potentially be packaged separately and mounted to a device (or connection) as required, it is advantageous for the device (or connection) to be packaged and sold as a single unit comprising the lever member mounted thereto.

The lever member may be mounted to or around the fluid transfer tip, especially if retrofitted to a conventional fluid transfer device or connection, as will be discussed further below. However this may risk the lever member taking up space around the fluid transfer tip that would better used to form the friction fit with a corresponding hub, or otherwise interfere with connection. In at least some embodiments it is therefore preferred that the lever member is mounted to a fluid chamber of the fluid transfer device or connection. Where the lever member comprises one or more side surfaces that extend in a direction substantially parallel to the axis of the fluid transfer tip, for example in a cylindrical or rectangular form, the side surface(s) may extend parallel to the fluid chamber for mounting purposes. Preferably the side surface(s) form a shroud extending from the fluid transfer tip to at least partially surround the fluid chamber and engage with mounting means provided by the fluid chamber.

The means for mounting the lever member may be integral with or separate from the fluid transfer tip. In one set of embodiments the fluid transfer device or connection includes integral means for mounting the lever member. In embodiments where the mounting means are integral with the fluid transfer tip, they may be positioned behind the fluid transfer tip, for example carried by a fluid chamber that is integrated with the tip. In one set of embodiments the fluid transfer device comprises a fluid chamber in communication with the fluid transfer tip and the mounting means is integrated with the fluid chamber. For example, the mounting means may comprise an axle integrated with the fluid chamber. In such examples, the fluid transfer device may comprise a syringe and the syringe barrel may have an axle moulded on its outer surface to pivotally mount the lever member. The fluid chamber, such as the barrel of a syringe, may therefore be designed to mount a lever member so that the device can be supplied with the lever member pre-mounted ready for use. In another set of embodiments the lever member could even be integrated with the fluid transfer device or connection, for example with the lever member pivotally mounted by an integral hinge. The lever member and fluid transfer device (or connection) could, for example, be formed as a single plastics moulding, e.g. with the lever member pivotally mounted by a living hinge or the like.

However, in another set of embodiments it may be desirable to retrofit a lever member to an existing fluid transfer device or connection. For example, it may be desirable to mount a lever member to a standard syringe or other device/connection so as to enjoy various of the benefits outlined above but without changing the design of the device/connection. In such embodiments it is preferable that the lever member is mounted by a separate attachment. The lever member may be attached to a fluid transfer device or connection by any suitable means. So as to avoid interference with the fluid transfer tip, the lever member may be attached to the aft end of the tip, or behind the tip, by an attachment collar.

It will be understood that such a retrofitting mechanism may be attached around the fluid transfer tip or any other part of a fluid transfer connection or device, such as a syringe, in any situation where operation of the lever member may assist in locking and subsequently disconnecting a hub to/from the tip. The mechanism may be attached before or after inserting the tip into a hub. Such a mechanism could be optionally attached to a fluid transfer device or connection by a user when it is determined that the friction fitting is too tight to be easily disconnected by pulling the tip away from the hub, or at least not without risking damage or injury. The mechanism could also be optionally attached where the fluid transfer device (or connection) is connected to a hub carrying a needle and protection from needle spike is desired.

In one set of embodiments it is preferable that the lever member is removably mounted to the device or connection. This means that a user may remove and discard the lever member if it is not required or if it is preferable to operate the device (or connection) without any interference from the lever member. Preferably the lever member is mounted in a bi-stable position such that a force above a certain threshold and/or in a certain direction must be applied to release it from its mounted position. This can prevent the lever member from being accidentally released from the device (or connection).

The Applicant has recognised that even when the lever member is resiliently biased so that the collar is normally closed around the fluid transfer tip to form a screw fit, there is a risk of a user accidentally operating the lever member and disconnecting a hub unintentionally. During some fluid transfer procedures it may be paramount to ensure that the fluid connection is not released inadvertently. This may be particularly dangerous during high pressure fluid transfer. One way of avoiding this could be to disable the lever member. For example, the fluid transfer device or connection may include means for locking the lever member so that it cannot be pivoted. A user may need to actively unlock the lever member before it can be moved. Another solution could be to remove the lever member i.e. reverting to a traditional Luer lock connection that has to be manually unscrewed.

A solution that ensures a high level of safety for the Luer lock connection, without changing the lever disconnection mechanism, is to provide the hub with means for locking the lever member. Thus in a set of embodiments the hub comprises a socket having a tapered internal surface to form the friction fitting, a screw thread around an outer surface of the socket to form the screw fit, and a flange circumscribing the screw thread so as to lock the screw fit.

There is further disclosed a hub for directing fluid from a fluid transfer connection, the hub comprising a socket having a tapered internal surface to form a friction fit with a corresponding fluid transfer tip inserted therein, a screw thread around an outer surface of the socket to enable a screw connection in addition to the friction fit, and a flange circumscribing the screw thread so as to lock the screw connection with a corresponding fluid transfer tip.

It will be appreciated that the extra flange circumscribing the screw thread of the hub can be arranged to engage against an outer surface of an internally threaded collar that forms a screw fit with the hub i.e. the Luer lock collar of a fluid transfer device or connection. Where the collar is mounted on a lever member, this engagement means that the lever member is immobilised so that it cannot be operated to release the screw fit. The hub may be designed so that the flange circumscribes the screw thread at a distance that substantially matches the width of a standard Luer lock collar. This distance may be chosen to provide an interference fit between the flange and a Luer lock collar. Alternatively, or in addition, the flange may be provided with an internal gripping surface, e.g. made of a material and/or coated or treated to increase the coefficient of friction with the outer surface of a Luer lock collar.

Thus in embodiments the hub may be connected to the fluid transfer tip of a fluid transfer device or connection, a friction fit being formed between the tip and the tapered internal surface of the socket, and a screw connection being formed between the screw thread and an internally threaded collar that at least partially surrounds the fluid transfer tip. Preferably the internally threaded collar is mounted on a lever member, the lever member being pivotally mounted to move relative to the fluid transfer tip to release the screw connection. The flange circumscribing the screw thread preferably engages an outer surface of the internally threaded collar so as to lock the screw connection against movement of the lever member. Thus the flange can prevent the internally threaded collar from moving or separating into multiple segments so that the screw connection cannot be released.

In other embodiments the fluid transfer tip of a fluid transfer device or connection may be connected to a hub that does not include such a flange. The hub may therefore allow a lever member to operate to move or separate an internally threaded collar that forms a screw connection/fit with the hub. In a set of embodiments the hub may comprise a tapered internal surface and an outer rim at its base, for example a standard Luer slip hub. The outer rim may form an interference fit with the internally threaded collar that is akin to a screw fit. In another set of embodiments the hub may comprise a tapered internal surface and an outer thread at its base, for example a standard Luer lock hub. The outer thread of such a hub is of course intended to form a screw fit with the internally threaded collar of a corresponding Luer lock fitting.

Furthermore, although the disclosure above relates to a screw thread or internally threaded collar being mounted on the lever member to form a screw fit with the hub, it will be appreciated that the disclosure extends to any latch or positive connection acting to lock the hub in addition to the normal friction fitting. For example, a suitable positive connection may be achieved by engaging a pair of male/female parts. Thus there is further disclosed a fluid transfer device or connection comprising: a fluid transfer tip, the fluid transfer tip comprising a tapered friction fitting for a corresponding hub; a lever member pivotally mounted to move relative to the fluid transfer tip; and a latch mounted on the lever member to engage a part mounted on the hub and provide a positive connection in addition to the friction fitting; wherein the hub is disconnected from the tip by pivoting the lever member to release the latch and to subsequently release the hub from the friction fitting. In some examples the latch may provide a positive connection on just one side of the fluid transfer tip, for example a latch extending up to 90° or up to 180° around the tip. In other examples the latch may provide a positive connection substantially all the way around the fluid transfer tip, for example a latch extending at least 180° or 270° and up to 360° around the tip. The latch may take the form of a screw thread or internally threaded collar. Any of the preferred features described above may equally be applied to this further disclosure.

It is also envisaged that suitable hubs may deviate from standard Luer slip or Luer lock designs. The Applicant has recognised that when a hub is to be disconnected using a lever member it may be helpful to provide space below the outer rim or thread for the lever member to interact with the hub. Thus in a set of embodiments the hub comprises a tapered internal surface and an outer rim or thread spaced from its base by a skirt portion. The skirt portion can conveniently provide room for a lever member to rotate before it comes into contact with the rim or thread. As is described above, this may allow an internally threaded collar to open to release the screw fit before further movement of the lever member moves a front surface (e.g. having a rim) forwards along the fluid transfer tip, past the skirt portion, to release the hub from the friction fitting by pushing against the rim or thread. The skirt portion may be flexible.

In at least some embodiments, the hub may further comprise an additional means for gripping a fluid transfer tip when the hub is connected thereto. For example, the additional means for gripping a tip may comprise a flange or groove provided on the tapered internal surface. The flange or groove on the inner surface of the hub may engage over a corresponding groove or flange when it is connected to a tip. Accordingly, such a corresponding groove or flange may be provided on the fluid transfer tip. For example, the hub may comprise an annular groove on its tapered internal surface and the fluid transfer tip may be circumscribed by an annular gripping flange.

During use, the hub may be connected to a fluid transfer tip provided by a fluid transfer device or connection in the form of a syringe, blood collection tube, hose, tubing, IV line, stopper or closing cone. The hub may take the form of any female Luer lock connector, for example including a fluid connection to a catheter, cannula or hypodermic needle. The fluid transfer device or connection may be arranged to transfer liquids and/or gases.

The fluid transfer device may comprise any type of device used to transfer fluid—liquid and/or gas—either to or from a fluid receptacle. The fluid receptacle may be inanimate or it may be part of a living subject, for example a bodily cavity, organ or vessel, such as a vein or artery. Although the present disclosure may find a wide range of uses, preferably the fluid transfer device is a medical device. The fluid transfer device may comprise one or more devices such as a syringe, pre-filled syringe, IV delivery device e.g. "drip", transfusion device, fluid pump, stopcock, aspirator, suction device, container for a blood collection tube or hose. The device may be made to meet the relevant medical standard(s), for example ISO 7886 for sterile hypodermic syringes.

BRIEF DESCRIPTION OF THE DRAWINGS

Some embodiments of the present invention will now be described, by way of example only, and with reference to the accompanying drawings, in which:

FIGS. 1a to 1d show an embodiment of a disconnecting mechanism for a syringe connected to a needle hub;

FIGS. 2a and 2b provide a side and a cross-sectional view of a conventional Luer slip hub;

FIGS. 3a and 3b provide a side and a cross-sectional view of a conventional Luer lock hub;

FIGS. 4a to 4e show another embodiment of a disconnecting mechanism for a syringe connected to a needle hub;

FIGS. 5a and 5b provide plan views showing an alternative to FIGS. 4c and 4d;

FIGS. 8a to 8c provide plan and perspective views showing an alternative version of the embodiment of FIG. 4;

FIGS. 9a to 9d illustrate some examples of a separable collar for use in the embodiments of FIGS. 4 to 7;

FIGS. 12a and 12b show another embodiment of a hub;

FIG. 13 shows another variant of a hub;

FIGS. 14a and 14b provide a side and a cross-sectional view of a different Luer lock hub;

FIGS. 15a and 15b provide perspective views of a hub connected to, and disconnected from, a syringe;

FIGS. 16a and 16b provide cross-sectional views of a first embodiment corresponding to FIGS. 15a and 15b;

FIG. 19 shows a disconnecting mechanism mounted to a fluid transfer tip at the end of a fluid transfer hose;

FIGS. 21a to 21d are cross-sectional views of the disconnecting mechanism during various stages of operation;

DETAILED DESCRIPTION

Figures 6A, 6B:
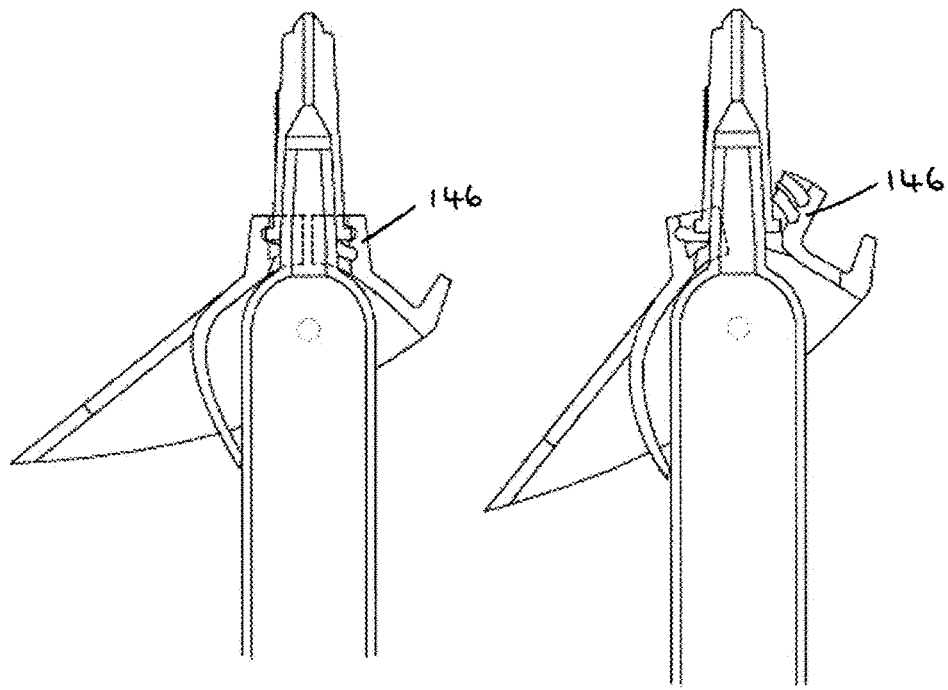
FIGS. 6a and 6b show a first variant of the embodiment of FIG. 4.

FIGS. 1a to 1d illustrate an embodiment of a disconnecting mechanism for a hub 10. The syringe 2 has a fluid transfer tip 6 that is tapered so as to form a Luer slip connection i.e. friction fitting with a corresponding hub 10. In addition the tip 6 may optionally be provided with an annular gripping flange 8 surrounding the tip 6 close to the barrel 4 of the syringe 2. The hub 10 may be a standard Luer slip hub 10 as seen in FIGS. 2a and 2b, or a hub 410 as seen in FIGS. 14a and 14b which includes an annular groove on its inner surface to grip onto the flange 8. The hub 10 may be similar to a standard Luer slip hub having an internal taper and an outer rim 12, except additionally provided with a skirt extending below the rim 12. Alternatively, the hub 10 may be a standard Luer lock hub 110 as seen in FIGS. 3a and 3b.

In this embodiment (see FIG. 1a) the syringe 2 has a pivotally mounted lever member 34 which carries a forwardly extending latch 46 in the form of a partial circular or semicircular collar carrying an internal screw thread 47. As is seen from FIGS. 1a and 1b, the hub 10 may be connected to the tip 6 by pushing it onto the friction fitting at the same time as twisting the hub 10 to connect (e.g. the rim 12) with the thread(s) 47 of the latch 46. If the hub 10 is not rotated then it may still be pushed along the tip 6, forcing the lever member 34 to pivot against its resilient bias, and then finally rotated to form a screw fit. In its resiliently biased position, seen in FIG. 1c, the lever member 34 is pivoted to keep the thread(s) 47 of the latch 46 positively engaged with the outer rim 12 of the hub 10. Although a two-handed operation may be required to connect the hub 10 to the syringe 2, the lever member 34 can be used to disconnect the hub 10 in a continuous, single-handed movement. FIG. 1d shows the lever member 34 being pivoted down against the resilient bias of its leaf spring 40 so that the threaded latch 46 is moved away from the hub 10 so that it no longer assists in holding the hub in a locked position. Pivotal movement of the lever member 34 also pushes the hub 10 out of engagement with the gripping flange 8 on the tip 6 and releases the friction fitting. The lever member 34 includes an actuator portion 45, positioned behind the latch 46 and provided by a front surface, that moves along the tip and pushes against the base of the hub 10 to release the friction fitting. It may be seen that, as the lever member 34 pivots, the actuator portion 45 tends to move into contact with the hub 10 after the screw thread(s) 47 of the latch 46 have moved out of engagement with the rim 12. However, the actuator portion 45 may not be solely responsible for releasing the friction fitting. In at least some embodiments the screw thread(s) 47 of the latch 46, which are typically helical or inclined, may push against the base of the hub 10 while the latch 46 is pivoting away from the tip 6. This may have the effect of at least partially releasing the friction fitting by pushing the hub 10 forwards along the tip 6 by a small distance. The degree to which such loosening occurs may, in practice, depend on the dimensions of the tapered friction fitting and/or how far the hub 10 is initially pushed onto the tapered friction fitting e.g. by a user. An optional catch member 44 is provided to prevent the hub 10 from flying away from the syringe 2. The catch member 44 only comes into engagement with the hub 10 once the lever member 34 is fully depressed and the friction fitting has been released.

In these embodiments the outer rim 12 of a standard Luer slip hub 10 is twisted to form a screw fit with an internal thread mounted on the latch 46 of the lever member 34. However a Luer slip hub is not usually intended to form a screw fit with a fluid transfer tip in the same way as a Luer lock connector. A Luer lock hub has an outer thread rather than a flat rim so as to ensure that a screw fit connection is made. FIGS. 2 and 3 compare conventional hubs. FIGS. 2a and 2b show a standard Luer slip hub 10 having an outer rim 12. FIGS. 3a and 3b show a standard Luer lock hub 110 having an outer thread 112. Either of these hubs 10, 110 may be connected to the fluid transfer tip 6 of the syringe 2 seen in FIGS. 1a-1d, the screw threads of the latch 46 engaging with either the rim 12 or outer thread 112 to provide a positive connection e.g. screw fit in addition to the friction fitting.

There will now be described some embodiments of a disconnecting mechanism for a standard Luer lock hub 110.

In FIGS. 4a-4e there is seen a syringe 102 that has a pivotably mounted lever member 134 resiliently biased by a leaf spring 140. The Luer lock hub 110 is connected to the tip 106 of the syringe 102 by a friction fitting between the tapered surfaces. The Luer lock hub 110 has an outer thread 112 at its base which enables the hub 110 to be connected by a screw fit in addition to the friction fitting. A conventional Luer lock syringe would provide an internally threaded collar that could be twisted onto the hub 110. However in these embodiments an internally threaded collar 146 is mounted on the lever member 134 and arranged to be split open when the lever member 134 is operated.

In order to connect or disconnect the hub 110 from the tip 106, the lever member 134 may be moved against the resilient bias of the spring 140 so as to open the collar 146, as is seen in FIG. 4b. It is no longer necessary to rotate the syringe 102 or the hub 110 when connecting or disconnecting. The screw connection is simply released when the lever member 134 is pressed down. When disconnecting the syringe 102 from the hub 110, it may not even be necessary to forcibly separate the friction fitting. As the lever member 134 is pivoted against the syringe 102 its front surface, or a rim on the front surface, may provide an actuator portion to push forwards along the tip 106 so as to push away the hub 110 and automatically separate the connection in a single one-handed operation, as is seen in FIG. 4c. An optional catch member 144 may be arranged to prevent the hub 110 from flying off. Further details of such a lever mechanism may be found in the Applicant's published application WO 2013/164358, the contents of which are hereby incorporated by reference.

When the lever member 134 is released, it automatically pivots under the resilient bias of the spring 140 so that the threaded collar 146 closes around the outer thread 112 of the Luer lock hub 110. Unlike the collar seen in FIG. 1, the threaded collar 146 can extend substantially 360° around the circumference of the Luer lock hub 110. This ensures the integrity of the screw fit providing the Luer lock connection. The plan views of FIGS. 4d and 4e demonstrate how, in one example, the threaded collar 146 splits apart into two semicircular segments when the lever member 134 is operated. Of course the threaded collar 146 may separate into multiple parts that move radially outwardly from one another when the collar is opened. These partly circular or semicircular e.g. arcuate segments may not be equal in circumference. An example of a threaded collar 246 that separates into three segments is shown in the plan views of FIGS. 5a and 5b.

Figures 7A, 7B:
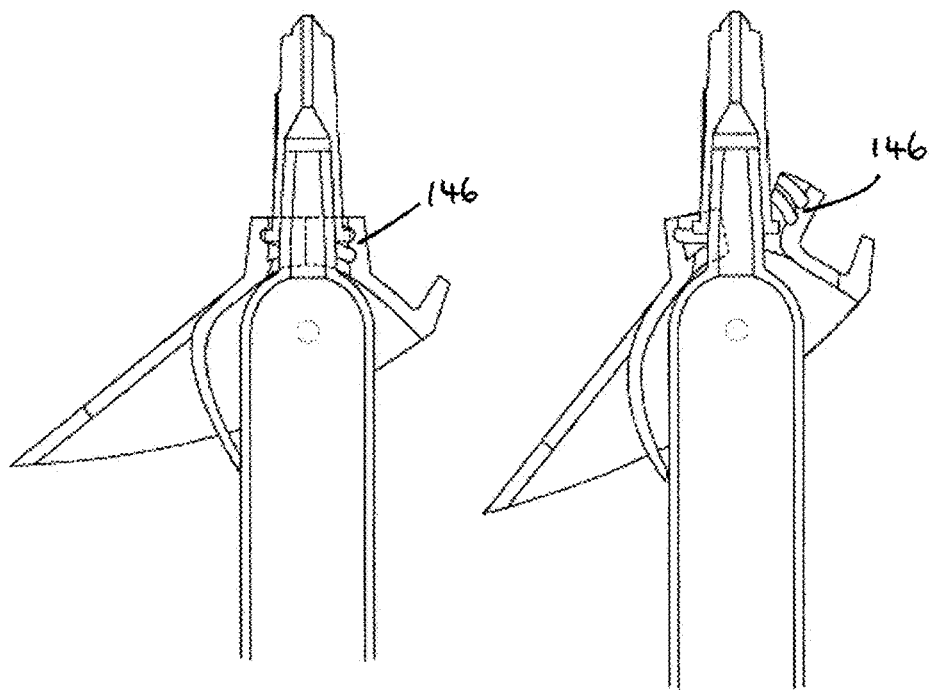
FIGS. 7a and 7b show a second variant of the embodiment of FIG. 4.

It will be appreciated that when the threaded collar 146 is closed around the hub 110, its segments may not exactly touch one another, for example as seen in FIGS. 6a and 6b. In one example, seen in FIGS. 7a and 7b, the threaded collar 146 forms a continuous 360 degree thread around the Luer lock hub 110.

When the lever member 134 is operated, the internally threaded collar 146 may separate into multiple segments that separate radially parallel to the lever member 134. In other embodiments, for example as shown in FIGS. 8a to 8c, a lever member 134 may carry an internally threaded collar 146 that separates into multiple segments that spread apart radially in a direction transverse to the lever member 134.

Figure 9A:
Figure 9C:
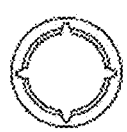
Figure 9D:
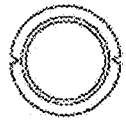

In any of these embodiments, the internally threaded collar 146 may already be separated into separate segments, for example a cut collar as seen in FIG. 9a. Alternatively, the threaded collar 146 may be formed as an integral 360° circle around the tip 106, but with one or more areas of weakness or frangible lines that enable the collar to split apart into multiple segments when a force is applied to the lever member 134. FIGS. 9b to 9d illustrate some possible examples.

Figure 10A:
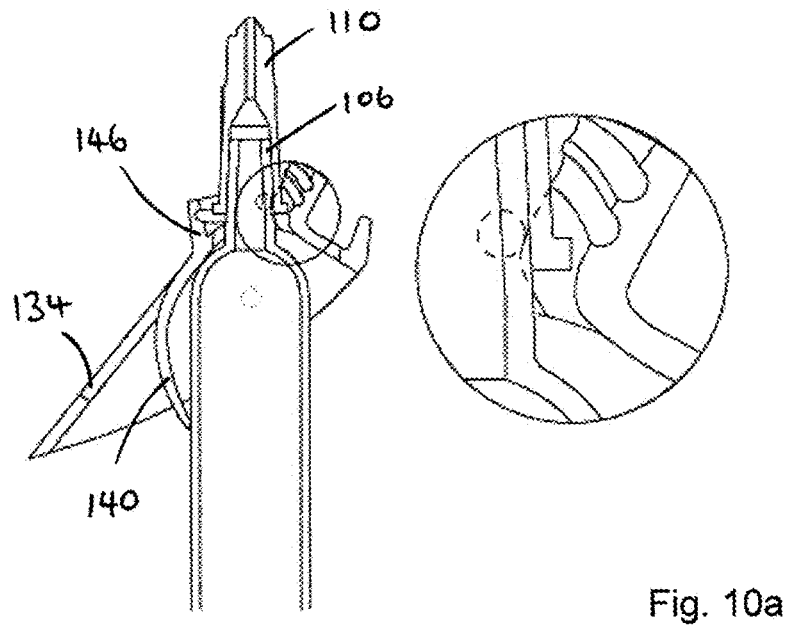
FIGS. 10a and 10b illustrate third and fourth variants of the embodiment of FIG. 4.
Figure 10B:
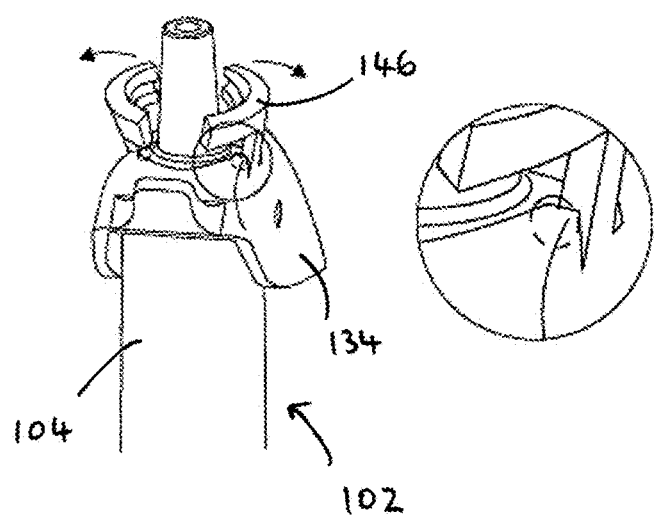

It will be appreciated that the lever member 134 may operate to split open the threaded collar 146 in any suitable way. In the illustrated example of FIG. 10a, a feature on the tip 106 is arranged to push against one or more of the segments of the threaded collar 146 when the lever member 134 is operated. In the illustrative example of FIG. 10b, a feature provided on the barrel 104 of the syringe 102 may act to push open the threaded collar 146 when the lever member 134 is operated.

Figure 11A:
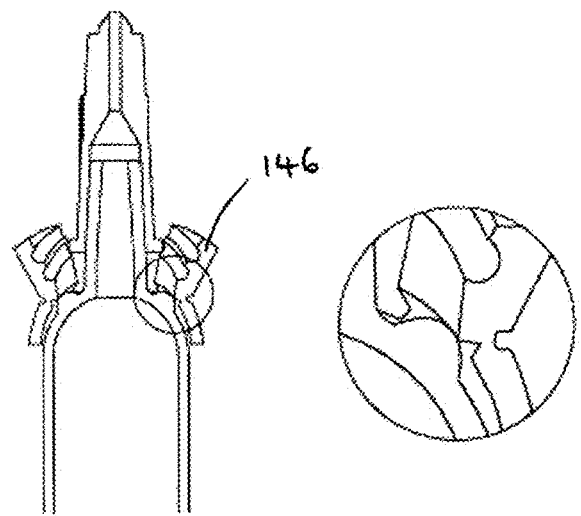
FIGS. 11a and 11b illustrate fifth and sixth variants of the embodiment of FIG. 4.
Figure 11B:
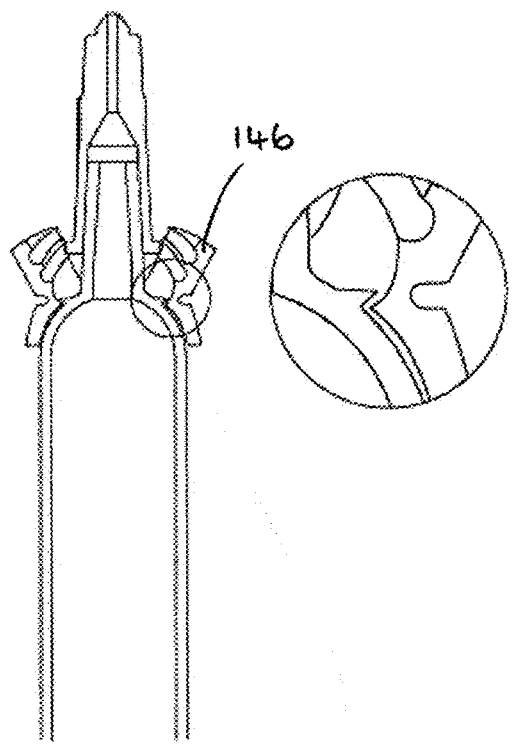

In at least some of these embodiments it is envisaged that the lever member 134 may be operated multiple times so as to open and close the threaded collar 146 and allow multiple connection and disconnection events to take place. However, in a medical setting where fluid transfer devices such as syringes are typically intended to only be used once, it can be desirable for the disconnecting mechanism to render the device unusable after a single use. FIGS. 11a and 11b illustrate some possible ways of achieving this. In FIG. 11a it is seen that the segments of the threaded collar 146 become permanently deformed upon operation of the lever member, so that the collar cannot be used again. FIG. 11b shows an alternative design where the segments of the collar 146 become locked in an open position once the lever member has operated.

It is an advantage of the embodiments described above that a standard Luer lock hub 110 can be connected and disconnected using the one-hand operation of a lever member. The resilient bias acting on the lever member ensures that its default position holds the threaded collar closed around the hub 110 and a user must purposely apply pressure to the lever member in order to unlock the connection. Even in the absence of a resilient bias, for example the leaf spring 40 being omitted, the lever member has a first position in which the screw thread(s) engage the hub with a screw fit in addition to the friction fitting. However, there may be some circumstances where a syringe or other fluid transfer device that carries such a lever member is to have a Luer lock connection with a hub, but without any risk of a user accidentally operating the lever member and opening the screw fit connection. In such situations, a standard Luer lock hub may be replaced with a novel locking hub 210 as seen in FIGS. 12a and 12b. In addition to the external thread 212, the hub 210 includes a circumferential flange 214 that circumscribes the screw thread 212. As is seen from FIG. 12b, this hub 210 may be connected to the tip 106 of a syringe 102 by twisting the screw thread 212 into engagement with the internally threaded collar 146 so that the outer flange 214 surrounds the collar 146 and therefore locks a screw connection. Even if pressure is applied to the lever member 134, it is not able to pivot and open the collar 146 due to the circumscribing flange 214 provided by the hub 210. The only way that a user can disconnect the hub 210 from the tip is by unscrewing it in the same way as a conventional Luer lock connection.

A similar type of locking flange may also be provided on a Luer slip hub. In another variant seen in FIG. 13, the lever member 334 is provided with an outwardly facing latch member 366, such as a partial circular or semicircular collar, that can lock inside the flange 314 of the hub 310.

Another hub 410 is shown in FIGS. 14a and 14b. It may be seen that the hub 410 carries an external thread 412, which means that the hub 410 may be used with a standard Luer lock connection if desired. The thread 412 may be omitted or replaced by a plain rim, in other variants. However, as compared to a conventional Luer lock hub (seen in FIGS. 3a and 3b), the hub 410 comprises a skirt 414 below the thread 412. The skirt 414 extends downwardly so as to pass through the slot in the front surface of the lever member. The skirt 414 therefore provides a surface that helps the lever member to engage the hub 410. It can further be seen from the cross-section shown in FIG. 14b that the skirt 414 has an annular groove 416 formed on its inner surface in addition to being tapered. The groove 416 provides an additional means for the hub 410 to be gripped when connected to a fluid transfer tip by a friction fitting, in particular a fluid transfer tip circumscribed by an annular gripping flange. Finally, it can also be seen from FIGS. 14a and 14b that the hub 410 may optionally include an outer ring 418 which is an ergonomic feature making it easier for a user to push the hub 410 onto a tip. Such a hub 410 may be connected/disconnected to/from the fluid transfer tip 6, 106 of a syringe 2, 102 as described above in relation to FIGS. 1-12.

FIGS. 15-18 illustrate some further embodiments of a locking and disconnecting mechanism for a hub 510, seen here as a standard Luer slip hub 510 carrying a flange 512. The hub 510 may be replaced by any of the other hubs described above. The hub 510 may carry a needle (not shown) or form part of a fluid transfer connection. The syringe 502 has a fluid transfer tip 506 that is tapered to form a Luer slip i.e. friction fitting with the hub 510. Behind the fluid transfer tip 506, a lever member 534 is pivotally mounted to the barrel 504 of the syringe 502. The lever member 534 carries a latch 546 in form of a screw thread or internally threaded collar. The lever member 534 can be manually operated to move the latch 546 between different positions.

As is seen in FIG. 15a, in a first position the lever member 534 is pivoted down so that the screw thread of the latch 546 engages the flange 512 of the hub 510 and thereby assists in holding the hub in a locked position. As is seen in FIG. 15b, in a second position the lever member 534 is pivoted up so that the screw thread does not engage the hub 510 and, furthermore, the lever member 534 acts to release the hub 510 from the friction fitting by an actuator portion 535 provided by a front surface pushing the hub 510 forwards along the tip 506. In this example, the actuator portion 535 extends through 180° around the tip 506 in a bottom half of the front surface. The latch 546 is an internally threaded collar that extends through 180° around the top 506 in a top half of the front surface. Although a two-handed operation may be required to connect the hub 510 to the syringe 502, the lever member 534 can be used to disconnect the hub 510 in a continuous, single-handed movement. As seen in the cross-sectional views of FIGS. 16a and 16b, an optional catch member 544 may be provided on the lever member 534 to prevent the hub 510 from flying away from the syringe 502 when it is released by movement into the second position.

Figure 17A:
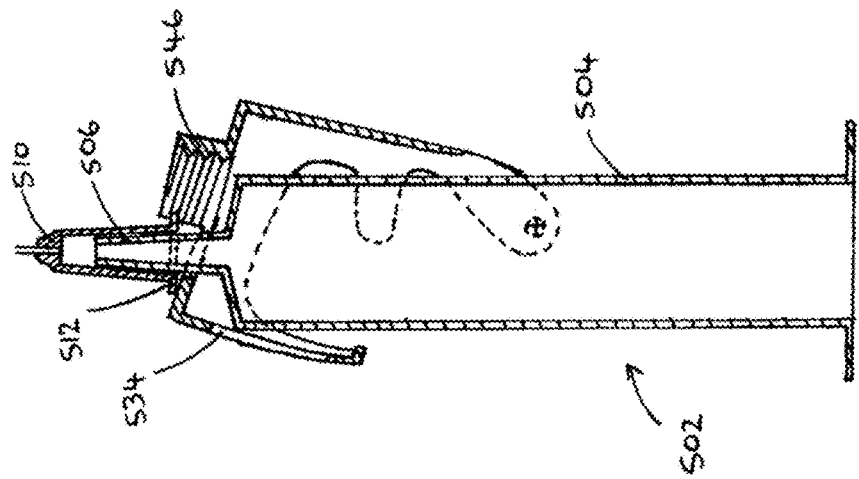
FIGS. 17a and 17b provide cross-sectional views of a second embodiment corresponding to FIGS. 15a and 15b.
Figure 17B:
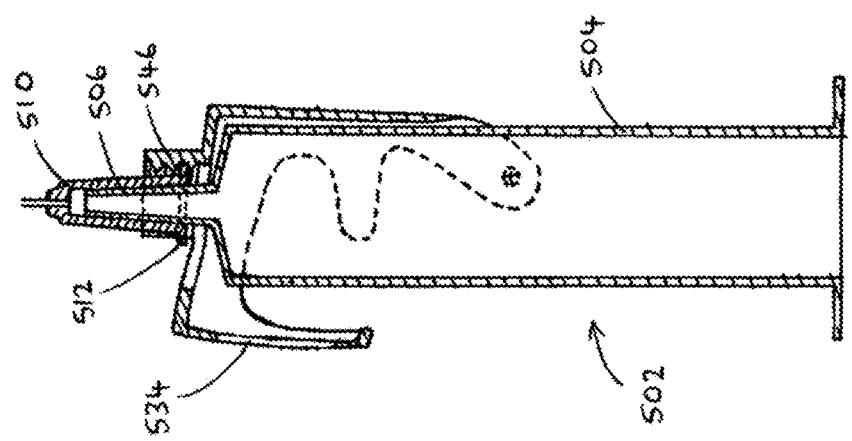
Figure 18B:
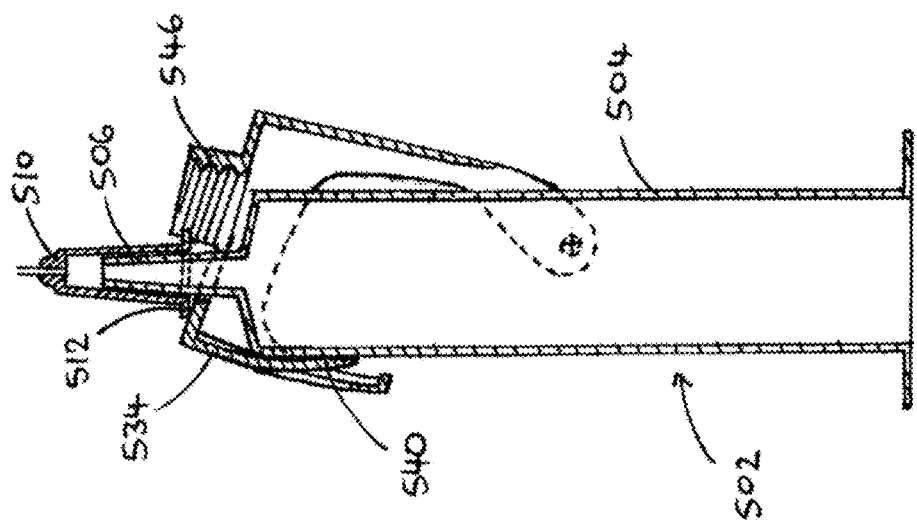
FIGS. 18a and 18b provide cross-sectional views of a third embodiment corresponding to FIGS. 15a and 15b.
Figure 18A:
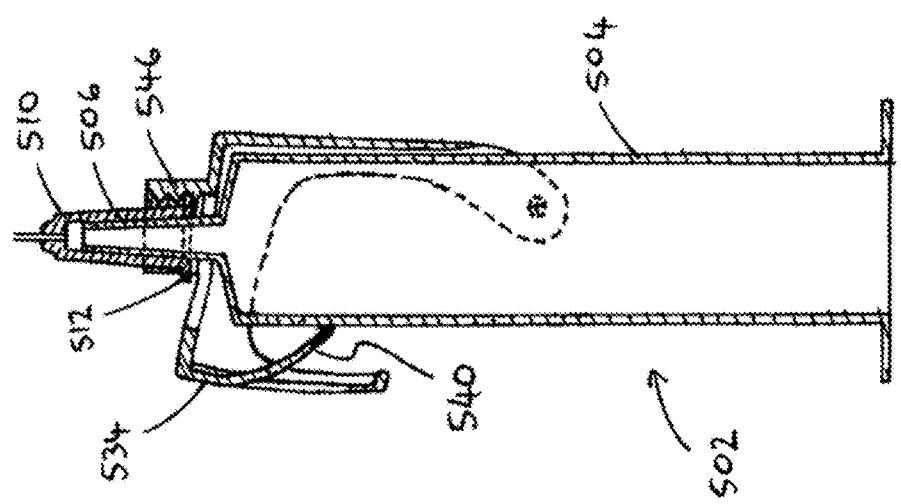

The lever member 534 may be freely pivotable between the first and second positions seen in FIGS. 15a and 15b. The cross-sectional views of FIGS. 17a and 17b show movement of the lever member 534 between the first (locking) position and the second (releasing and disconnecting) position. Alternatively, the lever member 534 may be resiliently biased into the first position e.g. by a leaf spring 540 (or other spring member), as seen in the cross-sectional views of FIGS. 18a and 18b. In this example a user must pivot the lever member 534 against the resilient bias of the leaf spring 540 in order to move the latch 546 away from the hub 510 and push the hub 510 along the tip 506, thereby releasing the friction fitting. It will be appreciated that a leaf spring or other form or resilient bias, where provided, may interact with the lever member on the same side of the device as the latch or on an opposite side or in any other suitable way.

Of course various embodiments, such as those described above, are not limited to a fluid transfer device in the form of a syringe. It will be appreciated that the disconnecting mechanisms described herein are not limited to use with a syringe comprising a barrel as a fluid chamber, but may instead be mounted to a fluid transfer tip at the end of a hose, pipe, cannula, etc. FIG. 19 shows a lever-actuated disconnection mechanism 2' mounted to a fluid transfer tip 6 at the end of a fluid transfer hose 35. Equally, such a hose or other fluid transfer device could replace the syringe shown in any of the other embodiments described above. Although the lever member 34' seen in FIG. 19 is not illustrated as including an internally threaded collar or other latch, as described in relation to the foregoing embodiments, the lever member 34' is pivotally mounted relative to the fluid transfer tip 6. It will be understood that an internally threaded collar or other latch may be added to this disconnection mechanism 2' such that it functions in the same way as described above, to disconnect a hub from the tip 6 at the end of a fluid transfer operation taking place via the hose 35 rather than the barrel of a syringe. Furthermore, although the disconnection mechanism 2' seen in FIG. 19 includes a leaf spring 40 to provide the lever member 34' with a resilient bias, this is an optional feature. And furthermore, although the disconnection mechanism 2' seen in FIG. 19 includes a catch member 44, this is also optional. For example, such a catch member 44 may be beneficial when disconnecting a needle hub, but another hub, Luer adaptor or connector part connected to the fluid transfer tip 6 may simply lead to a further hose or pipe. The disconnection mechanism 2' provides a user-friendly, single-handed action for disconnecting two Luer parts in a fluid transfer system without requiring an unscrewing action. This is a completely new approach to disconnecting Luer parts or adaptors fitted between fluid transfer hoses or between a hose and a fluid transfer device such as a cannula, catheter, IV line or syringe.

Figure 20:
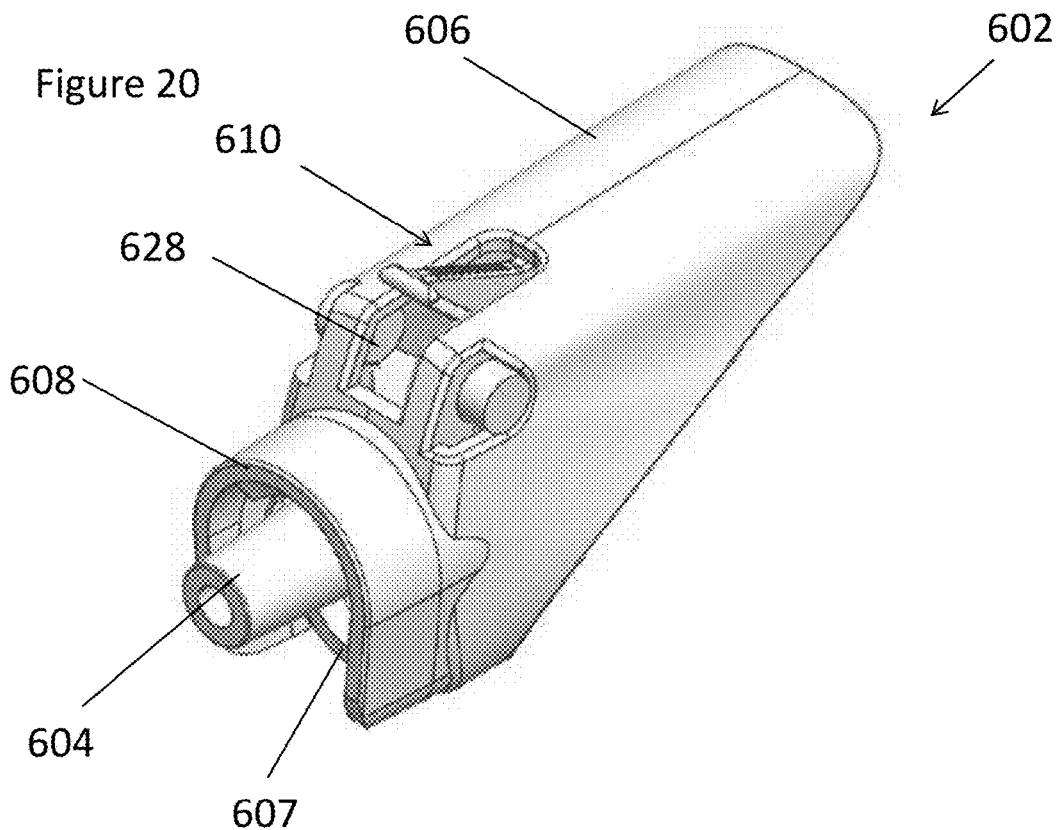
FIG. 20 is a perspective view of a disconnecting mechanism mounted to a fluid transfer tip.

FIG. 20 shows a perspective view of a further embodiment of a disconnecting mechanism 602 in accordance with an embodiment of the present invention. The disconnecting mechanism 602, similarly to previous embodiments, is mounted to or comprises a fluid transfer tip 604 having a tapered surface to form a friction fit with a corresponding connector part (not shown). The fluid transfer tip 604 may be at the end of a fluid transfer hose (not shown), for example as seen in FIG. 19. The disconnecting mechanism 602 comprises a lever member 606 pivotally mounted relative to the fluid transfer tip 604 so as to be capable of pushing a connector part (not shown) along the fluid transfer tip 604 so as to release the friction fit between the connector part and the tip 604. A suitable connector part may be the hub 10 seen in FIGS. 2a-2b, the hub 110 seen in FIGS. 3a-3b, or the hub 410 seen in FIGS. 14a-14b. In the embodiment shown, the fluid transfer tip 604 is in the form of a male tapered tip. The lever member 606 comprises a threaded portion 608, projecting from a forward end of the lever member 606, for engagement with a connector part when a connector part e.g. hub is connected to the fluid transfer tip 604. The threaded portion 608 latches onto an outer rim or thread of the hub so as to form a screw fit, as previously described. The threaded portion 608 in this embodiment is an internally threaded collar that extends through 180° around the fluid transfer tip 604. The lever 606 also comprises an actuator portion 607, arranged behind the collar 608 on a front surface of the lever 606, that moves forward along the tip 604 when the lever member 606 is pivoted down. The actuator portion 607 acts to release the friction fit between a hub (not shown) and the tip 604, usually after the collar 608 has moved out of engagement with the hub.

The fluid transfer tip 604 is an integral part of a main body 612 (which can be seen in FIGS. 21a-d). The lever member 606 is pivotally mounted to the main body 612 of the disconnecting mechanism 602 to permit pivotal movement relative to the fluid transfer tip 604. Arranged between the main body 612 of the disconnecting mechanism 602 and the lever member 606 is a locking arrangement 610. The locking arrangement 610 may act to lock the lever member 606 in the locking position seen in FIG. 20, i.e. the position at which the internally threaded collar 608 positively engages with a hub when a hub is connected to the fluid transfer tip 604. This locking position may be understood to be a first pivotal position of the lever member 606. The locking arrangement 610 may also act to lock the lever member 606 in a depressed position, i.e. when the lever member 606 has pivoted relative to the tip 604 and the internally threaded collar 608 has, at least partially, been moved away from the fluid transfer tip 604. This further locking position may be understood to be a pivotal second position. As can be seen in FIG. 20, the locking arrangement 610 extends through an aperture 628 located at a forward end of the lever member 606.

Figure 21A:
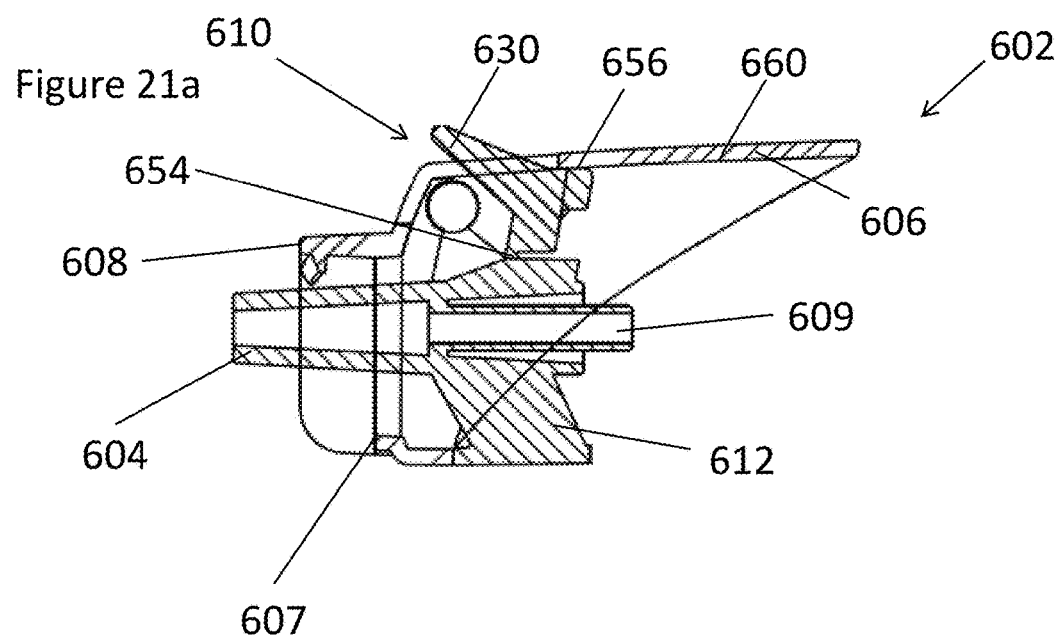

FIGS. 21a-21d show, in more detail, the release and locking of the locking arrangement 610. FIG. 21a shows a cross-sectional view, when viewed from the side, of the disconnecting mechanism 602, with the lever member 606 locked in the first position. The locking arrangement 610 comprises a locking member 630 which is attached to the main body 612 of the disconnecting mechanism 602, via a living hinge 654. The living hinge 654 allows the locking member 630 to pivot relative to the main body 612 and the lever member 606. The locking member 630 comprises a first locking surface 656 arranged to engage with an underside 660 of the lever member 606. In the position seen in FIG. 21a the first locking surface 656 engages with the underside 660 of the lever 606 and thereby prevents downwards pivotal movement of the lever member 606. The lever member 606 is thereby locked in its first pivotal position.

When a user wants to operate the lever member 606, e.g. when they wish to release a hub (not shown) from the fluid transfer tip 604, they must first release the engagement of the first locking surface 656 and the underside 660 of the lever member 606. This can be achieved, for example, by a user pushing forwards on the locking member 630, i.e. towards the fluid transfer tip 604, with their thumb. The forward force applied by a user will cause the locking member 630 to pivot about the living hinge 654. The locking member 630 must be pivoted by a sufficient amount to release the engagement between the first locking surface 656 and the underside 660 of the lever member 606. At this point, when the engagement between the first locking surface 656 and the underside 660 of the lever member 606 is released, the lever member 606 will be free to be pivoted downwards. This can be seen in FIG. 21b. It can be seen that the lever member 606 has not yet moved and the actuator portion 607 is in the same position as in FIG. 21a. A user may then begin to apply a force to the lever member 606 in order to disconnect a hub from the tip, as seen in FIGS. 21c and 21d.

Typically, as a user begins to apply a downwards force to the lever member 606 so as to cause its pivotal movement, they will often release the application of force to the locking member 630. The living hinge 654 may be resiliently biased, e.g. due to the material it is made from, and consequently when no force is applied by a user to the locking member 630, the living hinge 654 may tend to move back towards its natural position, which may for example correspond to the position seen in FIG. 21a. As a result of this movement, a rear surface 672, of the locking member 630, which links the first locking surface 656 and a second locking surface 658, will move into contact with an edge portion 674 of the of the aperture 628 on the lever member 606. Due to the contact between the rear surface 672 and the edge portion 674, the locking member 630 is prevented from moving completely backwards and thus ensures that the lever member 606 remains free to be pivoted by a user. FIG. 21c shows further progression of the lever member 606 through its pivotal motion. As the lever member 606 is pivoted further, the edge portion 674 moves towards the bottom of the rear surface 672 of the locking member 630. At the same time, the internally threaded collar 608 is moving away from the tip 604 so as to disengage from a hub connected to the tip 604. The actuator portion 607 starts to move forward along the tip 604.

As the lever member 606 is pivoted further, the edge portion 674 moves past the end of the rear surface 672, at which point the locking member 630 is able to pivot fully backwards under the resilient bias provided by the living hinge 654. In the embodiment shown, the locking member 630 comprises a second locking surface 658 and thus when the locking member 630 has pivoted fully backwards the second locking surface 658 engages with the top surface 652 of the lever member 606 and consequently the lever member 606 is locked in the depressed position, i.e. its second pivotal position. This locked position can be seen in FIG. 21d. In this second pivotal position the internally threaded collar 608 has completely pivoted away from the tip 604 such that it is no longer in engagement with a hub (not shown) and the actuator portion 607 has moved forwards along the tip 604 so as to release the hub from its friction fitting.

If a user wishes to release the lever member 606, and allow it to pivot back upwards into the first position, this can be achieved by applying a forward force to the locking member 630 to release the engagement between the second locking surface 658 and the top surface 662 of the lever member 606. Once the engagement has been released, the lever member 606 will be free to move back to its first pivotal position, i.e. moving back through the positions seen in FIGS. 21c and 21b to the first pivotal position in FIG. 21a. The lever member 606 may be manually moved back to the first pivotal position or alternatively it may be moved automatically under a resilient bias. In the embodiment shown, the lever member 606 is resilient biased into the first pivotal position by a resilient bias provided by deformation of the lever member itself. Whilst not shown explicitly in these Figures, as the lever member 606 is pivoted downwards into the second pivotal position, the lever member 606 is caused to deform, for example by protruding features on the side of the main body 612. As the lever member 606 may be made from a resilient material, e.g. plastic, once deformed the lever member 606 will provide its own resilient bias which tends to drive the lever member 606 into a position where it experiences no deformation, i.e. the first pivotal position.

As will be appreciated by those skilled in the art, due to the arrangement of the locking arrangement 610 at a forward end of the lever member 606, the disconnecting mechanism 602 may be used single handed, as a user may easily switch between operation of the locking arrangement 610 and the lever member 606, e.g. using only a thumb to apply a force to either the locking member 630 or the lever member 606. This may be advantageous in many applications such as medical procedures.

Whilst operation of the locking member 630 is discussed in relation to the disconnecting mechanism 602, it will be appreciated that the locking member 630 may be applied to any device or connection which employs a pivoting lever member. Additionally, whilst in the embodiment discussed above the locking member 630 takes the form of a pivoting member which pivots into and out of engagement with the lever member 606, it will be appreciated that the locking member 630 may take any other suitable form, for example a sliding member which slides into and out of engagement with the lever member 606.

Also seen in FIG. 21a is a fluid transfer passage 609 through the main body 612 in fluid communication with the tip 604. The passage 609 allows fluid to pass through the main body 612 of the disconnecting mechanism 602. The passage 609 may be connected to any fluid transfer component. For example, a user may manually connect flexible tubing to the passage 609 before use. A press fit or additional Luer-Slip or Luer-Lock connection may be used. Alternatively, flexible tubing may be permanently connected to the passage 609 and form part of the disconnecting mechanism. For example, flexible tubing may be welded or glued onto the end of the passage 609.

Figure 22:
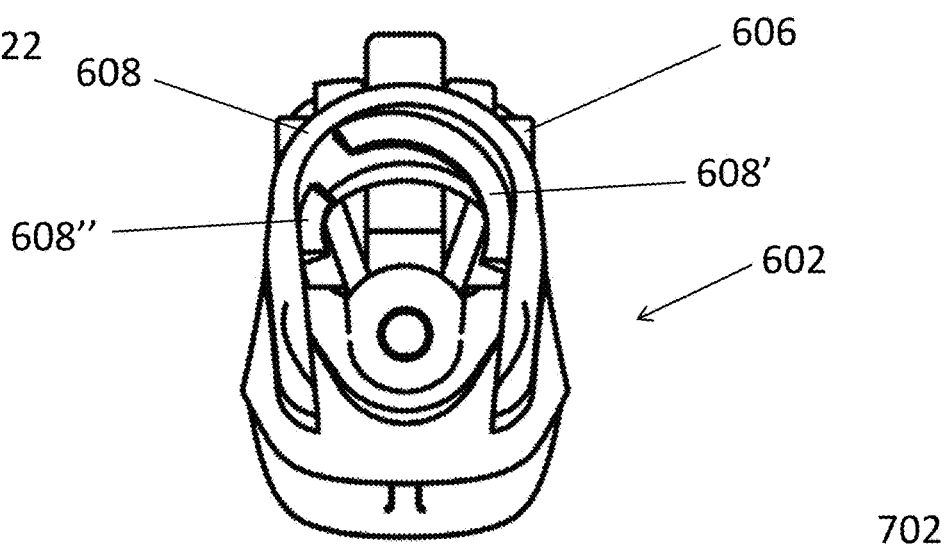
FIG. 22 shows a frontal view of the disconnecting mechanism seen in FIGS. 20 and 21.

FIG. 22 shows a frontal view of the disconnection mechanism 602 seen in FIG. 20 and FIGS. 21a-d. In this Figure, the lever member 606 is shown in the second pivotal position seen in FIG. 21d. As can be seen more clearly in this Figure, the internally threaded collar 608 comprises discrete threaded sections 608', 608". The threaded sections 608', 608" are sections of a helical thread. As will be appreciated, as the internally threaded collar 608 does not extend through 360°, the internal thread(s) provided thereon also cannot extend continuously through 360°. Accordingly, therefore, the thread is provided in two discrete threaded sections 608', 608" which are offset with respect to one another so that the threaded collar 608 may provide a threaded connection which grips onto multiple edges of a thread or rim on the outside of a hub that is connected to the tip.

Figure 23:
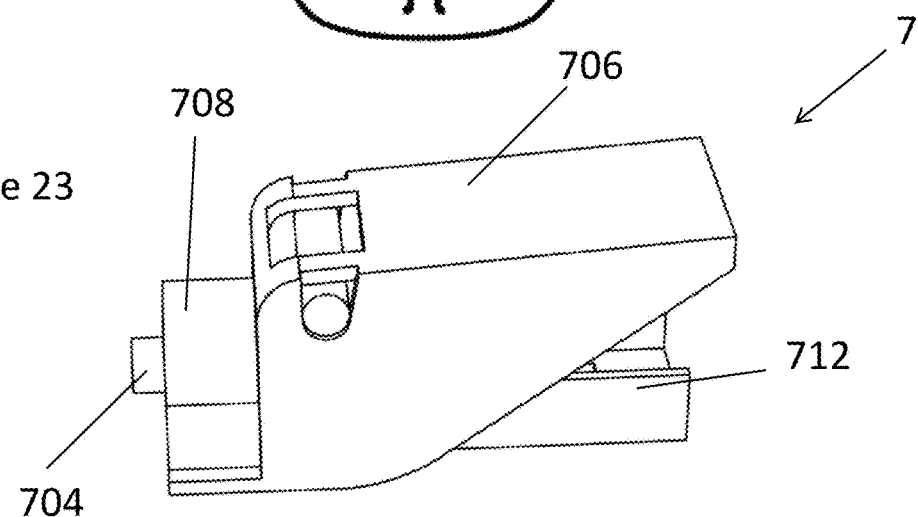
FIG. 23 is a perspective view of an alternative embodiment of a disconnecting mechanism mounted to a fluid transfer tip.

FIG. 23 shows a perspective view of another embodiment of a disconnecting mechanism 702 in accordance with an embodiment of the present invention. In this embodiment, instead of the locking arrangement being arranged on the top-side of the lever member, as is the case in the embodiment seen in FIGS. 20-22, the locking arrangement 710 is arranged on the underside of the disconnecting mechanism 702. This can be seen more clearly in FIG. 24. However, similarly to the disconnecting mechanism 602 seen in FIG. 20, the disconnecting mechanism 702 is mounted to or comprises a fluid transfer tip 704 having a tapered surface to form a friction fit with a corresponding connector part (not shown). The fluid transfer tip 704 may be at the end of a fluid transfer hose (not shown), for example as seen in FIG. 19. The disconnecting mechanism 702 comprises a lever member 706 pivotally mounted relative to the fluid transfer tip 704 so as to be capable of pushing a connector part e.g. hub (not shown) along the fluid transfer tip 704 so as to release a friction fit between the hub and the tip 704. A suitable connector part may be the hub 10 seen in FIGS. 2a-2b, the hub 110 seen in FIGS. 3a-3b, or the hub 410 seen in FIGS. 14a-14b. In the embodiment shown, the fluid transfer tip 704 is in the form of a male tapered tip. The lever member 706 comprises a threaded portion 708, projecting from a forward end of the lever member 706, for engagement with a hub when a hub is connected to the fluid transfer tip 704. The threaded portion 708 latches onto an outer rim or thread of the hub so as to form a screw fit, as previously described. The threaded portion 708 in this embodiment is an internally threaded collar that extends through 180° around the fluid transfer tip 704. The lever 706 also comprises an actuator portion 707 (not seen in this Figure), arranged behind the collar 708 on a front surface of the lever 706, that moves forward along the tip 704 when the lever member 706 is pivoted down. The actuator portion 707 acts to release the friction fitting between a hub (not shown) and the tip 704, usually after the collar 708 has moved out of engagement with the hub.

Figure 24:
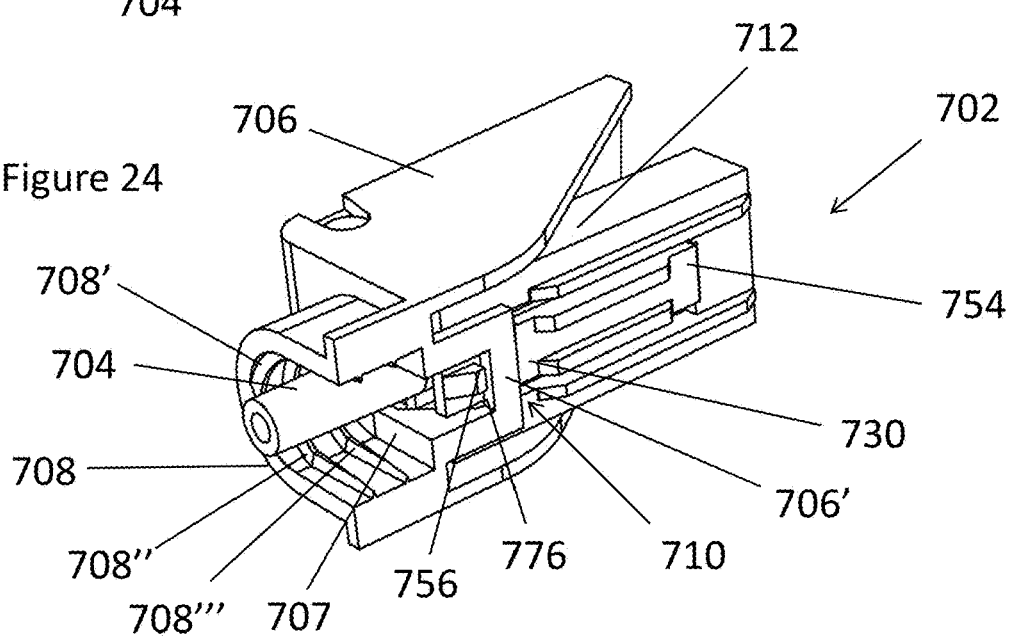
FIG. 24 is a view showing the underside of the disconnecting mechanism seen in FIG. 23.

The fluid transfer tip 704 is an integral part of a main body 712 (which can be seen in FIG. 24 and FIGS. 25a-d). The lever member 706 is pivotally mounted to the main body 712 of the disconnecting mechanism 702 to permit pivotal movement relative to the fluid transfer tip 704. Arranged between the main body 712 of the disconnecting mechanism 702 and the lever member 706 is the locking arrangement 710 which can be seen in FIG. 24. FIG. 24 shows a view of the underside of the disconnecting mechanism 702. In the embodiment shown, the locking arrangement 710 acts to lock the lever member 706 in the locking position seen in FIG. 23, i.e. the position at which the internally threaded collar 708 positively engages with a hub when a hub is connected to the fluid transfer tip 704. This locking position may be understood to be a first pivotal position of the lever member 706. In this particular embodiment, the locking arrangement 710 only acts to lock the lever member 706 in this first pivotal position, however it will be appreciated that the locking arrangement 710 may be modified so as to be capable of locking the lever member 706 in a second, pivotal position, as is the case with the embodiment seen in FIGS. 20-22.

As visible in FIG. 24, the lever member 706 extends around the main body 712 and defines a locking portion 706'. The locking portion 706' of the lever member 706 comprises an edge 776 onto which the locking arrangement 710 may engage. The locking arrangement 710 comprises a locking member 730 connected to the main body 712 via a living hinge 754. The locking member 730 is connected in such a way that it may be pressed, by a user, towards the main body 712 of the disconnecting mechanism 702, so as to release engagement with the locking portion 706' of the lever member 706. The forward end of the locking member defines a first locking surface 756 the interaction of which with the edge 776 will be described later, in more detail, in relation to FIGS. 25a-25d.

Also visible in FIG. 24 is the actuator portion 707 of the lever member 706 which acts to push a hub away from the fluid transfer tip 704, along with a plurality of discrete threaded sections 708', 708'', 708''' on an internal surface of the threaded collar 708 which engage with a hub to form a screw fit when a hub is connected to the fluid transfer tip 704.

It can be seen from FIGS. 25a-25d that the main body 712 integrally includes the fluid transfer tip 704 and a fluid transfer passage 709 in fluid communication with the tip 704. The fluid transfer passage 709 passes through the main body 712. The passage 709 may be connected to any fluid transfer component. For example, a user may manually connect flexible tubing to the passage 709 before use. A press fit or additional Luer-Slip or Luer-Lock connection may be used. Alternatively, flexible tubing may be permanently connected to the passage 709 and form part of the disconnecting mechanism. For example, flexible tubing may be welded or glued onto the end of the passage 709.

FIGS. 25a-25d show, in more detail, the release and locking of the locking arrangement 710. FIG. 21a shows a cross-sectional view, when viewed from the side, of the disconnecting mechanism 702, with the lever member 706 locked in the first pivotal position. The locking arrangement 710 comprising the locking member 730 can be seen. The locking member 730 attached to the main body 712 of the disconnecting mechanism 702, via the living hinge 754. The living hinge 754 allows the locking member 730 to flex relative to the main body 712 and the lever member 706. In this position, the first locking surface 756 of the locking member 730 engages with the edge 776 of the lever member 706. This engagement prevents downwards pivotal movement of the lever member 706 as the locking portion 706' is prevented from pivoting forwards towards the fluid transfer tip 704. The lever member 706 is thereby locked in its first pivotal position. In this position, the actuator portion 707 and the internally threaded collar 708 are locked in position.

Figure 25A:
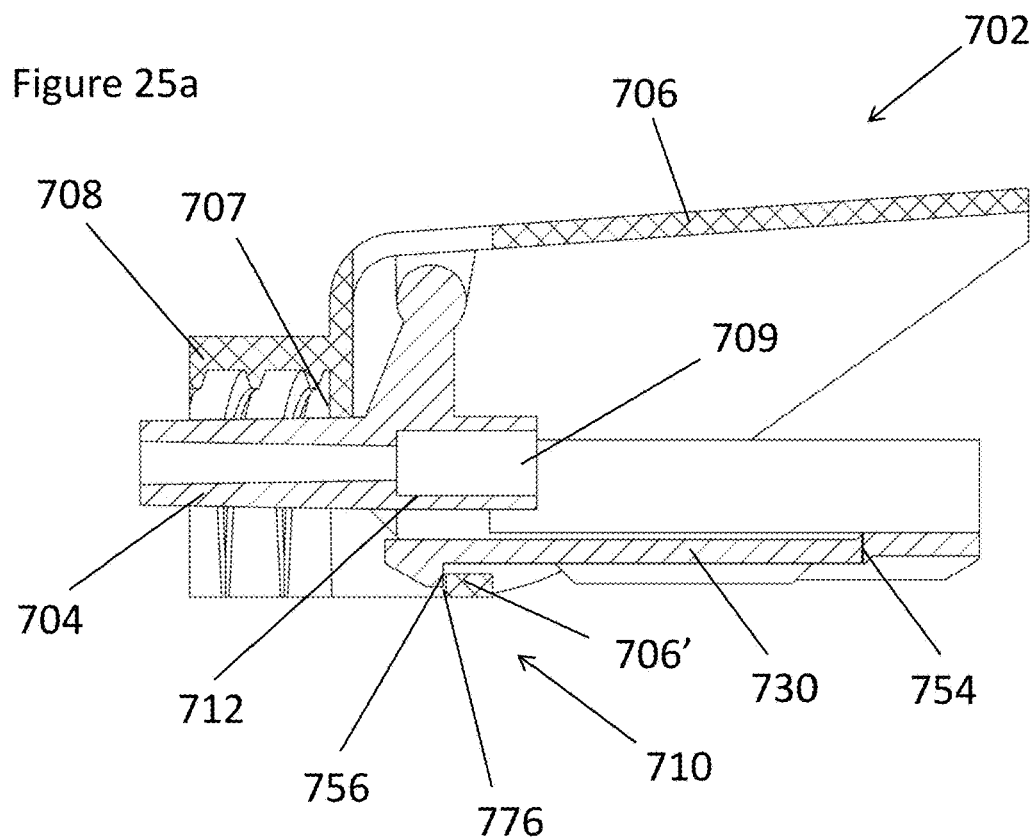
FIGS. 25a to 25d are cross-sectional views of the disconnecting mechanism of FIGS. 23 and 24 during various stages of operation.
Figure 25B:
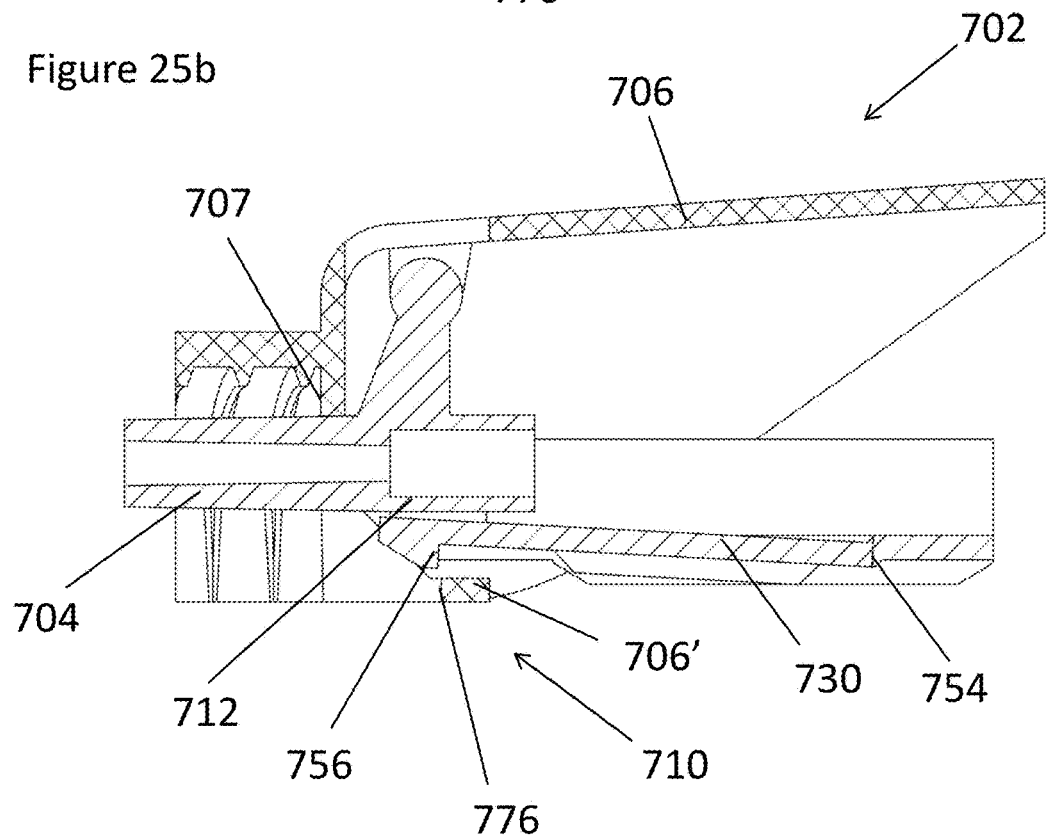

When a user wants to operate the lever member 706, e.g. when they wish to release a hub (not shown) from the fluid transfer tip 704, they must first release the engagement of the first locking surface 756 and the edge 776 of the locking portion 706' of the lever member 706. This can be achieved, for example, by a user pressing on the locking member 730, i.e. towards the fluid transfer tip 712, using their hand. Exactly how a user applies a pressing force to the locking member 730 will depend on how the disconnecting mechanism 702 is held by the user. The pressing force applied by a user will cause the locking member 730 to pivot about the living hinge 754 towards the main body 712. The locking member 730 must be pivoted by a sufficient amount to release the engagement between the first locking surface 756 and the edge 776 of the lever member 706. At this point, when the engagement between the first locking surface 756 and the edge 776 of the lever member 706 is released, the lever member 706 will be free to be pivoted downwards. This can be seen in FIG. 25b, in which it can be seen that the lever member 706 has not yet moved and the actuator portion 707 is in the same position as in FIG. 25a. Once the locking arrangement 710 has been disengaged, a user may then begin to apply a force to the lever member 706 in order to disconnect a hub from the tip, as seen in FIGS. 25c and 25d.

Figure 25C:
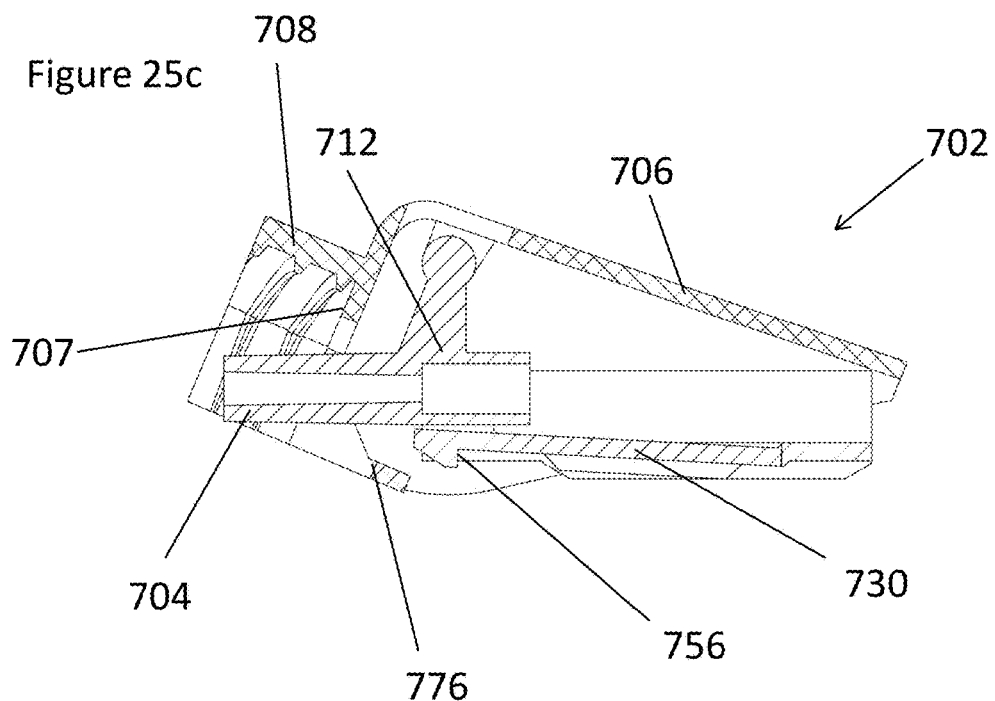
Figure 25D:
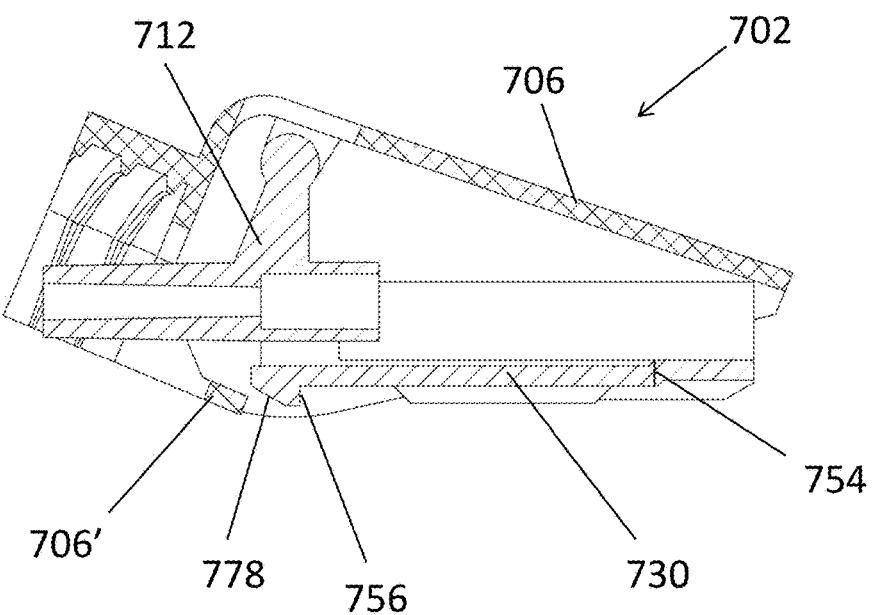

FIG. 25c shows the lever member 706 in the position at which it has been pivoted by the application of force by a user. In this particular instance, the locking member 730 remains held close to the main body 712, for example by the continuation of an applied pressing force by the user. As the lever member 706 is pivoted into the second pivotal position seen in FIG. 25c, the internally threaded collar 708 is moved away from the tip 704 so as to disengage from a hub connected to the tip 704. Additionally, the actuator portion 707 also starts to move forward along the tip 704 so as to disengage a hub connected to the tip 704. As shown, the edge 776 and the first locking surface 756 of the locking member 730 are not in engagement with one another.

Whilst applying a downwards force to the lever member 706 so as to cause its pivotal movement, or after the lever member 706 has been pivoted to its second pivotal position seen in FIG. 25c, a user may release any pressing force applied to the locking member 730. The living hinge 754 may be resiliently biased, e.g. due to the material it is made from, and consequently when no force is applied by a user to the locking member 730, the living hinge 754 may tend to move the locking member 730 back towards its natural position, which may for example correspond to the position seen in FIG. 25a. As a result of this movement the locking member 730 will be driven back towards the position seen in FIG. 25a. This state where the lever member 706 has been pivoted into its second pivotal position, and wherein the locking member 730 has been released and driven into its original position, can be seen in FIG. 25d.

The locking member 730 comprises, at its forward end proximal to the first locking surface 756, a chamfered surface 778. If a user wishes to release the lever member 706, and allow it to pivot back upwards into the first pivotal position, in this particular embodiment there is no requirement to unlock the lever member 706. Therefore, the lever member 706 will be free to move back from its second pivotal position to its first pivotal position, i.e. moving back through the positions seen in FIGS. 25c and 25b to the first position in FIG. 25a. The lever member 706 may be manually moved back to the first pivotal position or alternatively it may be moved automatically under a resilient bias. In the embodiment shown, the lever member 706 is resiliently biased into the first pivotal position by a resilient bias provided by deformation of the lever member itself. Whilst not shown explicitly in these Figures, as the lever member 706 is pivoted downwards into the second pivotal position, the lever member 706 is caused to deform, for example by protruding features on the side of the main body 712. As the lever member 706 may be made from a resilient material, e.g. plastic, once deformed the lever member 706 will provide its own resilient bias which tends to drive the lever member 706 into a position where it experiences no deformation, i.e. the first pivotal position. As the lever member 706 pivots back to its first pivotal position, seen in FIG. 25a, the locking portion 706' may come into contact with the chamfered surface 778 of the locking member 730. The chamfered surface 778 allows the lever member 706 to pivot back to its first pivotal position without the need for a user to interact with the locking member 730. As the locking portion 706' passes against the chamfered surface, it will act to displace the locking member 730 towards the main body 712, and thereby allow the lever member 706 to continue to pivot backwards. Once the locking portion 706' has passed over the chamfered surface 778, due to the resiliency provided by the living hinge 754, the locking member 730 will spring back to its first position, as seen in FIG. 25a, and the disconnecting mechanism 702 will once again become locked.

As will be appreciated by those skilled in the art, due to the arrangement of the locking arrangement 710 on the underside of the disconnecting mechanism 702, the disconnecting mechanism 702 may be gripped using a single hand, and thus be operated using a single hand. A user may easily switch between operation of the locking arrangement 710 and the lever member 706, e.g. by gripping the underside of the disconnecting mechanism 702 using their fingers, thereby releasing the locking arrangement 710 and applying a force to the lever member 706 using the palm of their hand. This may be advantageous in many applications such as medical procedures.

Whilst operation of the locking member 730 is discussed in relation to the disconnecting mechanism 702, it will be appreciated that the locking member 730 may be applied to any device or connection which employs a pivoting lever member. Additionally, whilst in the embodiment discussed above the locking member 730 takes the form of a pivoting member which pivots into and out of engagement with the locking portion 706' of the lever member 706, it will be appreciated that the locking member 730 may take any other suitable form, for example a sliding member which slides into and out of engagement with the lever member 706.

In any of the embodiments described above, the fluid transfer tip may have a tapered surface that is dimensioned so as to form a Luer connection according to ISO 80369-7, a NRFit® connection according to ISO 80369-6), or an ENFit connection according to ISO 80369-3. In any of the embodiments described above, the internally threaded portion e.g. collar may be dimensioned so as to form a Luer lock connection according to ISO 80369-7, a NRFit® connection according to ISO 80369-6), or an ENFit connection according to ISO 80369-3.

We claim:

1. A disconnecting mechanism comprising:
   a main body including:
      a fluid transfer tip having a tapered surface to form a friction fit with a corresponding connector part; and
      a fluid transfer passage in fluid communication with the fluid transfer tip and passing through the main body; and
   a lever member pivotally mounted to the main body, the lever member including:
      a threaded portion projecting from the lever member to enable the corresponding connector part to be connected to the fluid transfer tip by a screw fit in addition to the friction fit; and
      an actuator portion provided by a front surface of the lever member to actuate release of the friction fit;
   wherein, in a first pivotal position of the lever member, the threaded portion has a first position close to the fluid transfer tip to engage with an outer thread or rim of the corresponding connector part connected onto the fluid transfer tip and thereby form the screw fit in addition to the friction fit and, in a second pivotal position of the lever member, the threaded portion has a second position further away from the fluid transfer tip than the first position to disconnect the screw fit and the actuator portion is moved forwards along the fluid transfer tip to push away the corresponding connector part and thereby actuate release of the friction fit.

2. The disconnecting mechanism of claim 1, wherein the threaded portion projects forwards from the front surface of the lever member such that, in the first pivotal position of the lever member, the threaded portion is further forward along the fluid transfer tip than the actuator portion.

3. The disconnecting mechanism of claim 1, wherein the threaded portion is an internally threaded collar arranged such that, in the first pivotal position of the lever member, the collar surrounds the fluid transfer tip by up to 180°.

4. The disconnecting mechanism of claim 1, further comprising a hose connected to the fluid transfer passage.

5. The disconnecting mechanism of claim 1, further comprising a locking mechanism arranged between the main body and the lever member to prevent the lever member from moving out of the first pivotal position.

6. The disconnecting mechanism of claim 5, wherein the locking mechanism comprises a first locking surface that is engaged with the lever member when in the first pivotal position.

7. The disconnecting mechanism of claim 6, wherein the first locking surface is part of a locking member that is manually moveable to disengage the first locking surface from the lever member and allow the lever member to move out of the first pivotal position.

8. The disconnecting mechanism of claim 5, wherein the locking mechanism is further arranged to prevent the lever member from moving out of the second pivotal position.

9. The disconnecting mechanism of claim 8, wherein the locking mechanism comprises a second locking surface that is engaged with the lever member when in the second pivotal position.

10. The disconnecting mechanism of claim 9, wherein the second locking surface is part of said locking member, or another locking member, that is manually moveable to disengage the second locking surface from the lever member and allow the lever member to move out of the second pivotal position.

11. A fluid transfer device or fluid transfer connection comprising:
- a fluid transfer tip, the fluid transfer tip comprising a tapered friction fitting for a corresponding hub;
- a lever member pivotally mounted to move relative to the fluid transfer tip; and
- a screw thread mounted on the lever member to enable a hub to be connected to the tip by a screw fit in addition to the friction fitting;
- wherein the lever member is operable to move the screw thread between at least two different positions, wherein in a first position the screw thread engages the hub and in a second position the screw thread does not engage the hub and the lever member acts to release the hub from the friction fitting, and wherein the lever member is held with the screw thread in the first position and thereby assists in holding the hub in a locked position.

12. The fluid transfer device or fluid transfer connection of claim 11, further comprising gripping means arranged to hold the lever member in the first position.

13. The fluid transfer device or fluid transfer connection of claim 11, further comprising a locking arrangement for the lever member that requires a user to actively unlock the lever member before it can be pivoted to move the screw thread from the first position.

14. The fluid transfer device or fluid transfer connection of claim 11, further comprising a hose or tubing in fluid connection with the fluid transfer tip.

15. The fluid transfer device or fluid transfer connection of claim 11, wherein the lever member is manually operable to pivot and thereby move the screw thread between the first and second positions.

16. The fluid transfer device or fluid transfer connection of claim 11, wherein the lever member is operable to move the screw thread into a third position, between the first and second positions, where the screw thread no longer holds the hub in a locked position but the lever member allows the hub to remain connected to the fluid transfer tip by the friction fitting.

17. The fluid transfer device or fluid transfer connection of claim 11, wherein the lever member is resiliently biased to move the screw thread into the first position.

18. The fluid transfer device or fluid transfer connection of claim 11, further comprising means to lock the lever member against the resilient bias.

19. The fluid transfer device or fluid transfer connection of claim 11, further comprising a locking arrangement for the lever member, the locking arrangement including a locking member moveable to engage with the lever member and prevent the lever member from pivoting, such that the lever member is held with the screw thread in the first position.

20. The fluid transfer device or fluid transfer connection of claim 11, wherein the locking member is manually moveable by a user to actively unlock the lever member so that it can be pivoted.

* * * * *

UNITED STATES PATENT AND TRADEMARK OFFICE
CERTIFICATE OF CORRECTION

| | |
|---|---|
| PATENT NO. | : 10,258,785 B2 |
| APPLICATION NO. | : 15/892598 |
| DATED | : April 16, 2019 |
| INVENTOR(S) | : Christian Mide et al. |

It is certified that error appears in the above-identified patent and that said Letters Patent is hereby corrected as shown below:

On the Title Page

At item (63), after "Jul. 30, 2014-" add "and PCT/EP2013/066135 on Jul. 31, 2013", -before "now Pat. No. 9,889,259."

Signed and Sealed this
Eighteenth Day of June, 2019

Andrei Iancu
*Director of the United States Patent and Trademark Office*